(12) United States Patent
Emmitte

(10) Patent No.: US 7,560,568 B2
(45) Date of Patent: Jul. 14, 2009

(54) THIAZOLE COMPOUNDS

(75) Inventor: Kyle Allen Emmitte, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 302 days.

(21) Appl. No.: 10/587,328

(22) PCT Filed: Dec. 2, 2004

(86) PCT No.: PCT/US2004/040357

§ 371 (c)(1), (2), (4) Date: Jul. 24, 2006

(87) PCT Pub. No.: WO2005/075470

PCT Pub. Date: Aug. 18, 2005

(65) Prior Publication Data

US 2007/0066666 A1     Mar. 22, 2007

Related U.S. Application Data

(60) Provisional application No. 60/539,849, filed on Jan. 28, 2004.

(51) Int. Cl.
*A61K 31/427* (2006.01)
*C07D 417/04* (2006.01)

(52) U.S. Cl. .................. 548/181; 514/365; 514/369; 514/370

(58) Field of Classification Search .................. 548/181
See application file for complete search history.

(56) References Cited

U.S. PATENT DOCUMENTS

| 4,818,270 A | 4/1989 | Grabiak et al. |
| 4,988,689 A | 1/1991 | Janssens et al. |
| 5,545,653 A | 8/1996 | Miller et al. |
| 6,162,804 A | 12/2000 | Bilodeau et al. |
| 6,310,079 B1 | 10/2001 | Okumura et al. |
| 6,465,484 B1 | 10/2002 | Bilodeau et al. |

FOREIGN PATENT DOCUMENTS

| JP | 11-263788 A | 9/1999 |
| WO | WO-98/55120 A1 | 12/1998 |
| WO | WO-99/16755 A | 4/1999 |
| WO | WO-00/01676 A | 3/2000 |
| WO | WO-00/12089 A | 3/2000 |
| WO | WO-03/015776 A | 2/2003 |
| WO | W0-2004/014899 A | 2/2004 |

OTHER PUBLICATIONS

CA 69:67383, 1968.*
Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
Golub et al., Science, vol. 286, Oct. 15, 1999, pp. 531-537.*
J. Chan; The New World Health Organization Clasification of Lymphomas: The Past, The Present and The Future; Hematological Oncology; Jul. 2001; 19; 129-150; John Wiley & Sons Ltd.
M. Whitfield, et al.; Common Markers of Proliferation; Nature Reviews, Cancer; Feb. 2006; 6; 99-106; Nature Publishing Group.
N. Lee Harris, et al.; World Health Organization Classification of Neoplastic Diseases of the Hematopoietic and Lymphoid Tissues: Report of the Clinical Advisory Committee Meeting—Airlie House, VA, Nov. 1997; J. Clin. Oncology; Dec. 1999; 17(12); 3838-3849; American Soc. of Clin. Onc.

* cited by examiner

*Primary Examiner*—Laura L. Stockton
(74) *Attorney, Agent, or Firm*—Bonnie L. Deppenbrock

(57) ABSTRACT

The present invention provides compounds of formula (I):

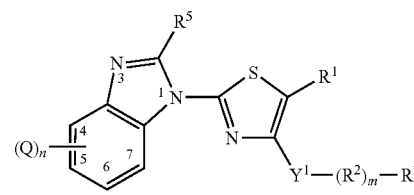

wherein all variables are as defined herein, pharmaceutical compositions containing the same, processes for preparing the same and their use as pharmaceutical agents.

17 Claims, No Drawings

THIAZOLE COMPOUNDS

CROSS REFERENCE TO RELATED APPLICATIONS

This application is a 371 Application of PCT/US2004/040357, filed 2 Dec. 2004, which claims priority to U.S. Application Ser. No. 60/539,849, filed 28 Jan. 2004.

BACKGROUND OF THE INVENTION

The present invention relates to novel compounds, pharmaceutical formulations comprising these compounds, and the use of these compounds in therapy. More particularly, the present invention relates to novel compounds and methods for treating conditions mediated by Polo-like Kinase, susceptible neoplasms, and other conditions.

Polo-like kinases ("PLK") are evolutionarily conserved serine/threonine kinases that play critical roles in regulating processes in the cell cycle. PLK plays a role in the entry into and the exit from mitosis in diverse organisms from yeast to mammalian cells. PLK includes PLK1, PLK2, and PLK3.

Polo-like kinases are known to be essential for mitosis in yeast, *Drosophila*, and *Xenopus*. For example, mutants of the homologous PLK genes in these organisms result in disordered mitotic spindles, and in *Drosophila* mutations can be embryonic lethal. RNA interference experiments on *Drosophila* polo have shown that ablation of polo in S2 cells results in G2/M arrest and apoptosis. PLK1 is the human homolog of *Drosophila* polo. It is believed to be involved in the entry into mitosis through the activation of cdk1 by phosphorylating and activating the phosphatase cdc25C, which in turn removes inhibitory phosphates from cdk1. This sets up an activation loop for cdk1 that leads to mitotic entry. PLK1 also phosphorylates cyclin B1, the cyclin partner of cdk1, resulting in nuclear localization. During mitosis, PLK1 has been shown to play roles in centrosome maturation and microtubule dynamics involved in formation of the mitotic spindle. PLK1 is also involved in the exit of cells from mitosis by phosphorylating and activating subunits of the anaphase-promoting complex (cdc16 and cdc27). PLK1 also phosphorylates cohesin proteins that hold sister chromatids together, exposing separase cleavage sites, and allowing separation of sister chromatids during anaphase. PLK1 may also play a role in cytokinesis through phosphorylation of the kinesin-like motor protein MKLP1. Inhibition of PLK1 thus has the potential to interfere with several stages of mitosis. Expression and activity of PLK protein increases during the cell cycle, reaching its peak during mitosis when it is also maximally phosphorylated. PLK1 mRNA is highly expressed in cells with a high mitotic index. PLK2 (serum-inducible kinase, SNK) and PLK3 (Proliferation-related kinase, PRK; Fibroblast Growth Factor-inducible kinase, FNK) were originally identified as immediate-early genes. PLK2 is not very well characterized, but PLK3 appears to be involved in regulation of cell cycle progression through M phase but functions differently from PLK1. Recent published work suggests that PLK3 plays an important role in the regulation of microtubule dynamics and function of the centrosome during mitosis.

Overexpression of PLK1 appears to be strongly associated with neoplastic cells (including cancers). A published study has shown high levels of PLK1 RNA expression in >80% of lung and breast tumors, with little to no expression in adjacent normal tissue. Several studies have shown correlations between PLK expression, histological grade, and prognosis in several types of cancer. Significant correlations were found between percentages of PLK-positive cells and histological grade of ovarian and endometrial cancer (P<0.001). These studies noted that PLK is strongly expressed in invading endometrial carcinoma cells and that this could reflect the degree of malignancy and proliferation in endometrial carcinoma. Using RT-PCR analysis, PLK overexpression was detected in 97% of esophageal carcinomas and 73% of gastric carcinomas as compared to the corresponding normal tissues. Further, patients with high levels of PLK overexpression in esophageal carcinoma represented a significantly poorer prognosis group than those with low levels of PLK overexpression. In head and neck cancers, elevated mRNA expression of PLK1 was observed in most tumors; a Kaplan-Meier analysis showed that those patients with moderate levels of PLK1 expression survived longer than those with high levels of PLK1 expression. Analysis of patients with non-small cell lung carcinoma showed similar outcomes related to PLK1 expression.

Disruption of mitosis with anti-microtubule drugs has been a successful approach in cancer chemotherapy. The taxanes and vinca alkaloids have been effectively used in the clinic, but they have undesirable side effects. In addition, many tumors appear to have weakened G2/M cell cycle checkpoints; in response to mitotic disruption these tumors attempt to bypass mitosis, leading to mitotic catastrophe and cell death. Several studies suggest that the disruption of mitosis by targeting PLK may be a feasible approach to selective tumor cell destruction. There remains a need in the art for new approaches to the treatment of neoplasms.

BRIEF SUMMARY OF THE INVENTION

According to a first aspect of the invention there is provided a compound of formula (I):

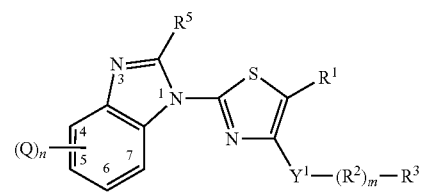

wherein:
$R^1$ is selected from —C(O)NR$^7$R$^8$ and —C(S)NR$^7$R$^8$;
$Y^1$ is selected from —O—, —S—, —NR$^7$—, —C=C— and —C≡C—;
m is 0 or 1;
n is 0, 1, 2, 3 or 4;
Q is a group of formula: —(R$^2$)$_a$—(Y$^2$)$_b$—(R$^2$)$_c$—R$^4$ or two adjacent Q groups are selected from alkyl, alkenyl, —OR$^7$, —S(O)$_f$R$^7$ and —NR$^7$R$^8$ and together with the carbon atoms to which they are bound, they form a C$_{5-6}$cycloalkyl, C$_{5-6}$cycloalkenyl, phenyl, 5-7 membered heterocycle having 1 or 2 heteroatoms selected from N, O and S, or 5-6 membered heteroaryl having 1 or 2 heteroatoms selected from N, O and S;
a, b and c are the same or different and are each independently 0 or 1;
$Y^2$ is selected from —O—, —S(O)$_f$—, —N(R$^7$)—, —C(O)—, —OC(O)—, —CO$_2$—, —C(O)N(R$^7$)—, —C(O)N(R$^7$)S(O)$_2$—, —OC(O)N(R$^7$)—, —OS(O)$_2$—, —S(O)$_2$N(R$^7$)—, —S(O)$_2$N(R$^7$)C(O)—, —N(R$^7$)S(O)$_2$—, —N(R$^7$)C(O)—, —N(R$^7$)CO$_2$— and —N(R$^7$)C(O)N(R$^7$)—;

each $R^2$ is the same or different and is independently selected from alkylene, alkenylene and alkynylene;

each $R^3$ and $R^4$ is the same or different and is each independently selected from H, halo, alkyl, alkenyl, alkynyl, —C(O)$R^7$, —C(O)NR$^7$R$^8$, —CO$_2$R$^7$, —C(S)R$^7$, —C(S)NR$^7$R$^8$, —C(=NR$^7$)R$^8$, —C(=NR$^7$)NR$^7$R$^8$, —CR$^7$=N—OR$^7$, —OR$^7$, —S(O)$_f$R$^7$, —S(O)$_2$NR$^7$R$^8$, —NR$^7$R$^8$, —N(R$^7$)C(O)R$^8$, —N(R$^7$)S(O)$_2$R$^8$, —NO$_2$, —CN, —N$_3$ and a group of formula (ii):

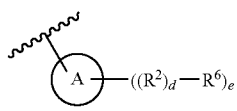

wherein:

Ring A is selected from $C_{5-10}$cycloalkyl, $C_{5-10}$cycloalkenyl, aryl, 5-10 membered heterocycle having 1, 2 or 3 heteroatoms selected from N, O and S and 5-10 membered heteroaryl having 1, 2 or 3 heteroatoms selected from N, O and S;

each d is 0 or 1;

e is 0, 1, 2, 3 or 4;

each $R^6$ is the same or different and is independently selected from H, halo, alkyl, alkenyl, alkynyl, cycloalkyl, cycloalkenyl, Ph, Het, —CH(OH)—R$^2$—OH, —C(O)R$^7$, —CO$_2$R$^7$, —CO$_2$—R$_2$-Ph, —CO$_2$—R$^2$-Het, —C(O)NR$^7$R$^8$, —C(O)N(R$^7$)C(O)R$^7$, —C(O)N(R$^7$)CO$_2$R$^7$, —C(O)N(R$^7$)C(O)NR$^7$R$^8$, —C(O)N(R$^7$)S(O)$_2$R$^7$, —C(S)R$^7$, —C(S)NR$^7$R$^8$, —C(=NR$^7$)R$^8$, —C(=NR$^7$)NR$^7$R$^8$, —CR$^7$=N—OR$^8$, =O, —OR$^7$, —OC(O)R$^7$, —OC(O)Ph, —OC(O)Het, —C(O)NR$^7$R$^8$, —O—R$^2$—S(O)$_2$R$^7$, —S(O)$_f$R$^7$, —S(O)$_2$NR$^7$R$^8$, —S(O)$_2$Ph, —S(O)$_2$Het, —NR$^7$R$^8$, —N(R$^7$)C(O)R$^8$, —N(R$^7$)CO$_2$R$^8$, —N(R$^7$)—R$^2$—CO$_2$R$^8$, —N(R$^7$)C(O)NR$^7$R$^8$, —N(R$^7$)—R$^2$—C(O)NR$^7$R$^8$, —N(R$^7$)C(O)Ph, —N(R$^7$)C(O)Het, —N(R$^7$)Ph, —N(R$^7$)Het, —N(R$^7$)C(O)NR$^7$—R$^2$—NR$^7$R$^8$, —N(R$^7$)C(O)N(R$^7$)Ph, —N(R$^7$)C(O)N(R$^7$)Het, —N(R$^7$)C(O)N(R$^7$)—R$^2$-Het, —N(R$^7$)S(O)$_2$R$^8$, —N(R$^7$)—R$^2$—S(O)$_2$R$^8$, —NO$_2$, —CN and —N$_3$;

Ph is phenyl optionally substituted from 1 to 3 times with a substituent selected from halo, alkyl, —OH, —R$^2$—OH, —O-alkyl, —R$^2$—O-alkyl, —NH$_2$, —N(H)alkyl, —N(alkyl)$_2$, —CN and —N$_3$;

Het is a 5-7 membered heterocycle having 1, 2, 3 or 4 heteroatoms selected from N, O and S, or a 5-6 membered heteroaryl having 1, 2, 3 or 4 heteroatoms selected from N, O and S, each optionally substituted from 1 to 2 times with a substituent selected from halo, alkyl, oxo, —OH, —R$^2$—OH, —O-alkyl, —R$^2$—O-alkyl, —NH$_2$, —N(H)alkyl, —N(alkyl)$_2$, —CN and —N$_3$;

wherein when $Y^1$ is —O—, —S— or —NR$^7$— and m is 0, then $R^3$ is not halo, —CO$_2$R$^7$, —C(S)R$^7$, —C(S)NR$^7$R$^8$, —C(=NR$^7$)R$^8$, —C(=NR$^7$)NR$^7$R$^8$, —CR$^7$=N—OR$^7$, —OR$^7$, —S(O)$_2$NR$^7$R$^8$, —NR$^7$R$^8$, —N(R$^7$)C(O)R$^8$, —N(R$^7$)S(O)$_2$R$^8$, —NO$_2$, —CN or —N$_3$;

wherein when Q is defined where b is 1 and c is 0, $R^4$ is not halo, —C(O)R$^7$, —C(O)NR$^7$R$^8$, —CO$_2$R$^7$, —C(S)R$^7$, —C(S)NR$^7$R$^8$, —C(=NR$^7$)R$^8$, —C(=NR$^7$)NR$^7$R$^8$, —CR$^7$=N—OR$^7$, —OR$^7$, —S(O)$_f$R$^7$, —S(O)$_2$NR$^7$R$^8$, —NR$^7$R$^8$, —N(R$^7$)C(O)R$^8$, —N(R$^7$)S(O)$_2$R$^8$, —NO$_2$, —CN or —N$_3$;

$R^5$ is selected from H, halo, alkyl, cycloalkyl, OR$^7$, —S(O)$_f$R$^7$, —NR$^7$R$^8$, —NHC(O)R$^7$, —NHC(O)NR$^7$R$^8$ and —NHS(O)$_2$R$^7$;

f is 0, 1 or 2; and each $R^7$ and each $R^8$ are the same or different and are each independently selected from H, alkyl, alkenyl, alkynyl, cycloalkyl and cycloalkenyl;

or a pharmaceutically acceptable salt, solvate or physiologically functional derivative thereof.

In another aspect of the invention there is provided a pharmaceutical composition comprising a compound of formula (I). In one embodiment, the pharmaceutical composition further comprises a pharmaceutically acceptable carrier, diluent or excipient.

In a third aspect of the invention, there is provided a method for treating a condition mediated by PLK in an animal. The method comprises administering to the animal a therapeutically effective amount of a compound of formula (I) or a pharmaceutically acceptable salt, solvate or physiologically functional derivative thereof.

In a fourth aspect of the invention, there is provided a method for treating a neoplasm susceptible to PLK in an animal. The method comprises administering to the animal a therapeutically effective amount of a compound of formula (I) or a pharmaceutically acceptable salt, solvate or physiologically functional derivative thereof. The susceptible neoplasm may be selected from breast cancer, colon cancer, lung cancer, prostate cancer, lymphoma, leukemia, endometrial cancer, melanoma, pancreatic cancer, ovarian cancer, squamous carcinoma, carcinoma of the head and neck, and esophageal carcinoma.

In a fifth aspect of the invention, there is provided a method for treating a PLK-mediated condition characterized by inappropriate cellular proliferation. The method comprises contacting the cell with a therapeutically effective amount of a compound of formula (I) or a pharmaceutically acceptable salt, solvate or physiologically functional derivative thereof.

In a sixth aspect, the present invention provides a method for inhibiting proliferation of a cell. The method comprises contacting the cell with an amount of a compound of formula (I) or a pharmaceutically acceptable salt, solvate or physiologically functional derivative thereof sufficient to inhibit proliferation of the cell, wherein the compound inhibits PLK.

In another aspect, the present invention provides a method for inhibiting mitosis in a cell. The method comprises administering to the cell an amount of a compound of formula (I) or a pharmaceutically acceptable salt, solvate or physiologically functional derivative thereof sufficient to inhibit mitosis in the cell, wherein the compound inhibits PLK.

In another aspect, there is provided a process for preparing a compound of formula (I) comprising the steps of:

a) reacting a compound of formula (III):

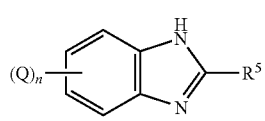

with a compound of formula (IV):

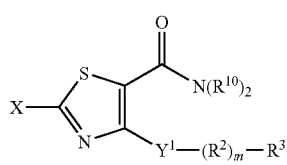

wherein:
X is Cl, Br or I;
each $R^{10}$ is the same or different and is selected from H, alkyl, alkenyl, alkynyl, cycloalkyl and cycloalkenyl;
to prepare a compound of formula (I);
b) optionally converting the compound of formula (I) to a pharmaceutically acceptable salt, solvate or physiologically functional derivative thereof; and
c) optionally converting the compound of formula (I) or a pharmaceutically acceptable salt, solvate or physiologically functional derivative thereof to a different compound of formula (I) or a pharmaceutically acceptable salt, solvate or physiologically functional derivative thereof.

In another aspect, the present invention provides a radiolabeled compound of formula (I) or a pharmaceutically acceptable salt, solvate or physiologically functional derivative thereof. In one embodiment, the present invention provides a tritiated compound of formula (I) or a pharmaceutically acceptable salt, solvate or physiologically functional derivative thereof. In another aspect, the present invention provides a biotinylated compound of formula (I) or a pharmaceutically acceptable salt, solvate or physiologically functional derivative thereof.

In another aspect, the present invention provides a compound of formula (I) or a pharmaceutically acceptable salt, solvate or physiologically functional derivative thereof for use in therapy.

In yet another aspect, the present invention provides a compound of formula (I) or a pharmaceutically acceptable salt, solvate or physiologically functional derivative thereof for use in the treatment of a condition mediated by PLK in an animal.

In yet another aspect, the present invention provides a compound of formula (I) or a pharmaceutically acceptable salt, solvate or physiologically functional derivative thereof for use in the treatment of a neoplasm susceptible to PLK in an animal.

In another aspect, the present invention provides a compound of formula (I) or a pharmaceutically acceptable salt, solvate or physiologically functional derivative thereof for use in the treatment of a PLK-mediated condition characterized by inappropriate cellular proliferation.

In yet another aspect, the present invention provides a compound of formula (I) or a pharmaceutically acceptable salt, solvate or physiologically functional derivative thereof for use in inhibiting proliferation of a cell, wherein the compound inhibits PLK.

In yet another aspect, the present invention provides a compound of formula (I) or a pharmaceutically acceptable salt, solvate or physiologically functional derivative thereof for use in inhibiting mitosis in a cell, wherein the compound inhibits PLK.

In yet another aspect, the present invention provides the use of a compound of formula (I) or a pharmaceutically acceptable salt, solvate or physiologically functional derivative thereof for the preparation of a medicament for the treatment of a condition mediated by PLK in an animal.

In yet another aspect, the present invention provides the use of a compound of formula (I) or a pharmaceutically acceptable salt, solvate or physiologically functional derivative thereof for the preparation of a medicament for the treatment of a neoplasm susceptible to PLK in an animal.

In yet another aspect, the present invention provides the use of a compound of formula (I) or a pharmaceutically acceptable salt, solvate or physiologically functional derivative thereof for the preparation of a medicament for the treatment of a PLK-mediated condition characterized by inappropriate cellular proliferation in an animal.

In yet another aspect, the present invention provides the use of a compound of formula (I) or a pharmaceutically acceptable salt, solvate or physiologically functional derivative thereof for the preparation of a medicament for inhibiting proliferation of a cell, wherein the compound is a PLK inhibitor.

In yet another aspect, the present invention provides the use of a compound of formula (I) or a pharmaceutically acceptable salt, solvate or physiologically functional derivative thereof for the preparation of a medicament for inhibiting mitosis in a cell, wherein the compound is a PLK inhibitor.

In yet another aspect, the present invention provides a pharmaceutical composition comprising a compound of formula (I) for use in the treatment of a neoplasm susceptible to PLK in an animal.

DETAILED DESCRIPTION OF THE INVENTION

As used herein, "a compound of the invention" or "a compound of formula (I)" means a compound of formula (I) or a pharmaceutically acceptable salt, solvate, or physiologically functional derivative thereof. Similarly, with respect to isolatable intermediates such as for example, compounds of formula (III), (IV) and (VII) the phrase "a compound of formula (number)" means a compound having that formula and pharmaceutically acceptable salts, solvates and physiologically functional derivatives thereof.

As used herein, the terms "alkyl" (and "alkylene") refer to straight or branched hydrocarbon chains containing from 1 to 8 carbon atoms. Examples of "alkyl" as used herein include, but are not limited to, methyl, ethyl, n-propyl, n-butyl, n-pentyl, isobutyl, isopropyl, and tert-butyl. Examples of "alkylene" as used herein include, but are not limited to, methylene, ethylene, propylene, butylene, and isobutylene. "Alkyl" also includes substituted alkyl. The alkyl groups may be optionally substituted one or more times with a halogen. Thus, the term "alkyl" includes trifluoromethyl and trifluoroethyl, among other halogenated alkyls.

As used herein, the term "alkenyl" refers to straight or branched hydrocarbon chains containing from 2 to 8 carbon atoms (unless a different number of atoms is specified) and at least one and up to three carbon-carbon double bonds. Examples of "alkenyl" as used herein include, but are not limited to ethenyl and propenyl. "Alkenyl" also includes substituted alkenyl. The alkenyl groups may optionally be substituted one or more times with a halogen.

As used herein, the term "alkynyl" refers to straight or branched hydrocarbon chains containing from 2 to 8 carbon atoms (unless a different number of atoms is specified) and at least one and up to three carbon-carbon triple bonds. Examples of "alkynyl" as used herein include, but are not limited to ethynyl and propynyl. "Alkynyl" also includes substituted alkynyl. The alkynyl groups may optionally be substituted one or more times with a halogen.

As used herein, the term "cycloalkyl" refers to a non-aromatic monocyclic carbocyclic ring having from 3 to 8 carbon atoms (unless a different number of atoms is specified) and no carbon-carbon double bonds. "Cycloalkyl" includes by way of example cyclopropyl, cyclobutyl, cyclopentyl, cyclohexyl, cycloheptyl and cyclooctyl. "Cycloalkyl" also includes substituted cycloalkyl. The cycloalkyl may optionally be substituted on any available carbon with one or more substituents selected from the group consisting of halo, $C_{1-3}$alkyl (including haloalkyl, e.g., perfluoroalkyl), —OH, —O—$C_{1-3}$alkyl, —$NH_2$, —NH($C_{1-3}$alkyl)-N($C_{1-3}$alkyl)$_2$, —CN and —$N_3$. Preferred cycloalkyl groups include $C_{3-6}$cycloalkyl and substituted $C_{3-6}$cycloalkyl.

As used herein, the term "cycloalkenyl" refers to a non-aromatic monocyclic carbocyclic ring having from 3 to 8 carbon atoms (unless a different number of atoms is specified) and up to 3 carbon-carbon double bonds. "Cycloalkenyl" includes by way of example cyclobutenyl, cyclopentenyl and cyclohexenyl. "Cycloalkenyl" also includes substituted cycloalkenyl. The cycloalkenyl may optionally be substituted on any available carbon with one or more substituents selected from halo, $C_{1-3}$alkyl (including haloalkyl, e.g., perfluoroalkyl), —OH, —O—$C_{1-3}$alkyl, —$NH_2$, —NH($C_{1-3}$alkyl), —N($C_{1-3}$alkyl)$_2$, —CN and —$N_3$.

The term "halo" or "halogen" refers to fluorine, chlorine, bromine and iodine.

The term "oxo" as used herein refers to the group =O attached directly to a carbon atom of a hydrocarbon ring (i.e., cycloalkenyl, aryl, heterocycle or heteroaryl ring) as well as —N-oxides, sulfones and sulfoxides wherein the N or S are atoms of a heterocyclic or heteroaryl ring.

The term "aryl" refers to monocyclic carbocyclic groups and fused bicyclic carbocyclic groups having from 6 to 13 carbon atoms (unless a different number of atoms is specified) and having at least one aromatic ring. Examples of particular aryl groups include but are not limited to phenyl and naphthyl. One particular aryl group according to the invention is phenyl.

The terms "heterocycle" and "heterocyclic" refer to monocyclic saturated or unsaturated non-aromatic groups and fused bicyclic saturated or unsaturated non-aromatic groups, having the specified number of members and containing 1, 2, 3 or 4 heteroatoms selected from N, O and S (unless a different number of heteroatoms is specified). Examples of particular heterocyclic groups include but are not limited to tetrahydrofuran, dihydropyran, tetrahydropyran, pyran, tetrahydropyran, thietane, 1,4-dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, tetrahydrothiophene, and the like.

The term "heteroaryl" refers to aromatic monocyclic groups and fused bicyclic groups wherein at least one ring is aromatic, having the specified number of members and containing 1, 2, 3, or 4 heteroatoms selected from N, O and S (unless a different number of heteroatoms is specified). Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole.

The term "members" (and variants thereof e.g., "membered") in the context of heterocyclic and heteroaryl groups refers to the total atoms, carbon and heteroatoms N, O and/or S, which form the ring. Thus, an example of a 6-membered heterocyclic ring is piperidine and an example of a 6-membered heteroaryl ring is pyridine.

As used herein, the term "optionally" means that the subsequently described event(s) may or may not occur, and includes both event(s) that occur and events that do not occur.

The present invention provides compounds of formula (I):

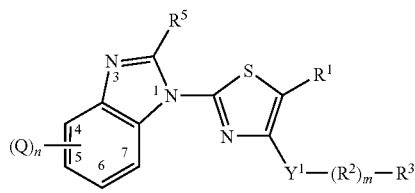

I wherein:
$R^1$ is selected from —C(O)$NR^7R^8$ and —C(S)$NR^7R^8$;
$Y^1$ is selected from —O—, —S—, —$NR^7$—, —C=C— and —C≡C—;
m is 0 or 1;
n is 0, 1, 2, 3 or 4;
Q is a group of formula: —$(R^2)_a$—$(Y^2)_b$—$(R^2)_c$—$R^4$ or two adjacent Q groups are selected from alkyl, alkenyl, —$OR^7$, —S(O)$_f R^7$ and —$NR^7R^8$ and together with the carbon atoms to which they are bound, they form a $C_{5-6}$cycloalkyl, $C_{5-6}$cycloalkenyl, phenyl, 5-7 membered heterocycle having 1 or 2 heteroatoms selected from N, O and S, or 5-6 membered heteroaryl having 1 or 2 heteroatoms selected from N, O and S;
a, b and c are the same or different and are each independently 0 or 1;
$Y^2$ is selected from —O—, —S(O)$_f$—, —N($R^7$)—, —C(O)—, —OC(O)—, —$CO_2$—, —C(O)N($R^7$)—, —C(O)N($R^7$)S(O)$_2$—, —OC(O)N($R^7$)—, —OS(O)$_2$—, —S(O)$_2$N($R^7$)—, —S(O)$_2$N($R^7$)C(O)—, —N($R^7$)S(O)$_2$—, —N($R^7$)C(O)—, —N($R^7$)$CO_2$— and —N($R^7$)C(O)N($R^7$)—;
each $R^2$ is the same or different and is independently selected from alkylene, alkenylene and alkynylene;
each $R^3$ and $R^4$ is the same or different and is each independently selected from H, halo, alkyl, alkenyl, alkynyl, —C(O)$R^7$, —C(O)$NR^7R^8$, —$CO_2R^7$, —C(S)$R^7$, —C(S)$NR^7R^8$, —C(=$NR^7$)$R^8$, —C(=$NR^7$)$NR^7R^8$, —$CR^7$=N—$OR^7$, —$OR^7$, —S(O)$_f R^7$, —S(O)$_2NR^7R^8$, —$NR^7R^8$, —N($R^7$)C(O)$R^8$, —N($R^7$)S(O)$_2R^8$, —$NO_2$, —CN, —$N_3$ and a group of formula (ii):

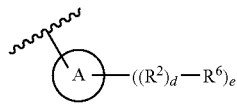

ii wherein:
Ring A is selected from $C_{5-10}$cycloalkyl, $C_{5-10}$cycloalkenyl, aryl, 5-10 membered heterocycle having 1, 2 or 3 heteroatoms selected from N, O and S and 5-10 membered heteroaryl having 1, 2 or 3 heteroatoms selected from N, O and S;
each d is 0 or 1;
e is 0, 1, 2, 3 or 4;
each $R^6$ is the same or different and is independently selected from H, halo, alkyl, alkenyl, alkynyl, cycloalkyl, cycloalkenyl, Ph, Het, —CH(OH)—$R^2$—OH, —C(O)$R^7$, —$CO_2R^7$, —$CO_2$—$R_2$-Ph, —$CO_2$—

R²-Het, —C(O)NR⁷R⁸, —C(O)N(R⁷)C(O)R⁷, —C(O)N(R⁷)CO₂R⁷, —C(O)N(R⁷)C(O)NR⁷R⁸, —C(O)N(R⁷)S(O)₂R⁷, —C(S)R⁷, —C(S)NR⁷R⁸, —C(=NR⁷)R⁸, —C(=NR⁷)NR⁷R⁸, —CR⁷=N—OR⁸, =O, —OR⁷, —OC(O)R⁷, —OC(O)Ph, —OC(O)Het, —C(O)NR⁷R⁸, —O—R²—S(O)₂R⁷, —S(O)ᵢR⁷, —S(O)₂NR⁷R⁸, —S(O)₂Ph, —S(O)₂Het, —NR⁷R⁸, —N(R⁷)C(O)R⁸, —N(R⁷)CO₂R⁸, —N(R⁷)—R²—CO₂R⁸, —N(R⁷)C(O)NR⁷R⁸, —N(R⁷)—R²—C(O)NR⁷R⁸, —N(R⁷)C(O)Ph, —N(R⁷)C(O)Het, —N(R⁷)Ph, —N(R⁷)Het, —N(R⁷)C(O)NR⁷—R²—NR⁷R⁸, —N(R⁷)C(O)N(R⁷)Ph, —N(R⁷)C(O)N(R⁷)Het, —N(R⁷)C(O)N(R⁷)—R²-Het, —N(R⁷)S(O)₂R⁸, —N(R⁷)—R²—S(O)₂R⁸, —NO₂, —CN and —N₃;

Ph is phenyl optionally substituted from 1 to 3 times with a substituent selected from halo, alkyl, —OH, —R²—OH, —O-alkyl, —R²—O-alkyl, —NH₂, —N(H)alkyl, —N(alkyl)₂, —CN and —N₃;

Het is a 5-7 membered heterocycle having 1, 2, 3 or 4 heteroatoms selected from N, O and S, or a 5-6 membered heteroaryl having 1, 2, 3 or 4 heteroatoms selected from N, O and S, each optionally substituted from 1 to 2 times with a substituent selected from halo, alkyl, oxo, —OH, —R²—OH, —O-alkyl, —R²—O-alkyl, —NH₂, —N(H)alkyl, —N(alkyl)₂, —CN and —N₃;

wherein when $Y^1$ is —O—, —S— or —NR⁷— and m is 0, then $R^3$ is not halo, —C(O)R⁷, —C(O)NR⁷R⁸, —CO₂R⁷, —C(S)R⁷, —C(S)NR⁷R⁸, —C(=NR⁷)R⁸, —C(=NR⁷)NR⁷R⁸, —CR⁷=N—OR⁷, —OR⁷, —1S(O)ᵢR⁷, —S(O)₂NR⁷R⁸, —NR⁷R⁸, —N(R⁷)C(O)R⁸, —N(R⁷)S(O)₂R⁸, —NO₂, —CN or —N₃;

wherein when Q is defined where b is 1 and c is 0, $R^4$ is not halo, —C(O)R⁷, —C(O)NR⁷R⁸, —CO₂R⁷, —C(S)R⁷, —C(S)NR⁷R⁸, —C(=NR⁷)R⁸, —C(=NR⁷)NR⁷R⁸, —CR⁷=N—OR⁷, —OR⁷, —S(O)ᵢR⁷, —S(O)₂NR⁷R⁸, —NR⁷R⁸, —N(R⁷)C(O)R⁸, —N(R⁷)S(O)₂R⁸, —NO₂, —CN or —N₃;

$R^5$ is selected from H, halo, alkyl, cycloalkyl, OR⁷, —S(O)ᵢR⁷, —NR⁷R⁸, —NHC(O)R⁷, —NHC(O)NR⁷R⁸ and —NHS(O)₂R⁷;

f is 0, 1 or 2; and each $R^7$ and each $R^8$ are the same or different and are each independently selected from H, alkyl, alkenyl, alkynyl, cycloalkyl and cycloalkenyl;

and pharmaceutically acceptable salts, solvates and physiologically functional derivatives thereof.

In one embodiment, the compounds of formula (I) are defined wherein $R^1$ is —C(O)NR⁷R⁸. In one embodiment, the compounds of formula (I) are defined wherein $R^1$ is selected from —C(O)NH₂, —C(O)N(H)alkyl, —C(O)N(alkyl)₂, —C(S)NH₂, —C(S)N(H)alkyl and —C(S)N(alkyl)₂, or any subset thereof. In one embodiment, $R^1$ is selected from —C(O)NH₂, —C(O)N(H)alkyl, —C(S)NH₂ and —C(S)N(H)alkyl, or any subset thereof. In one embodiment, $R^1$ is selected from —C(O)NH₂ and —C(S)NH₂, or any subset thereof. In one particular embodiment, $R^1$ is —C(O)NH₂.

In one embodiment, the compounds of formula (I) are defined wherein $Y^1$ is selected from —O—, —S— and —N(R⁷)—, or any subset thereof. In another embodiment, $Y^1$ is selected from —O— and —N(R⁷)—. In one particular embodiment, $Y^1$ is —O—. In another particular embodiment, $Y^1$ is —N(R⁷)— and $R^7$ is H or alkyl, more particularly H.

m is 0 or 1. In one embodiment, the compounds of formula (I) are defined wherein m is 0. In the embodiment wherein m is 1 and thus the $(R^2)_m$ group is present, $R^2$ is typically alkylene or alkenylene, more particularly alkylene. In one particular embodiment, m is 1 and $(R^2)_m$ is $C_{1-3}$alkylene.

Consistent with the definition of $Y^1$ and m, the group $R^3$ may be selected from H, halo, alkyl, alkenyl, alkynyl, —C(O)R⁷, —C(O)NR⁷R⁸, —CO₂R⁷, —C(S)R⁷, —C(S)NR⁷R⁸, —C(=NR⁷)R⁸, —C(=NR⁷)NR⁷R⁸, —CR⁷=N—OR⁷, —OR⁷, —S(O)ᵢR⁷, —S(O)₂NR⁷R⁸, —NR⁷R⁸, —N(R⁷)C(O)R⁸, —N(R⁷)S(O)₂R⁸, —NO₂, —CN, —N₃ and a group of formula (ii):

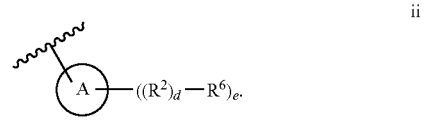

ii

In one embodiment, $R^3$ is selected from H, alkyl, alkenyl, alkynyl, and a group of formula (ii), or any subset thereof. In one particular embodiment, $R^3$ is selected from H, alkyl, alkenyl and alkynyl, or any subset thereof. In one embodiment, when $R^3$ is alkyl, $R^3$ is $C_{2-6}$alkyl.

In one particular embodiment, $R^3$ is a group of formula (ii).

in formula (ii) is referred to herein as "Ring A." Ring A is selected from $C_{5-10}$cycloalkyl, $C_{5-10}$cycloalkenyl, aryl, 5-10 membered heterocycle having 1, 2 or 3 heteroatoms selected from N, O and S and 5-10 membered heteroaryl having 1, 2 or 3 heteroatoms selected from N, O and S. Ring A may be bonded to $R^2$, or $Y^1$ (when m is 0) through any suitable carbon or heteroatom. In one embodiment, the compounds of formula (I) are defined wherein $R^3$ is a group of formula (ii) and Ring A is selected from $C_{5-10}$cycloalkyl, $C_{5-10}$cycloalkenyl, aryl, 5-10 membered heterocycle having 1, 2 or 3 heteroatoms selected from N, O and S and 5-10 membered heteroaryl having 1, 2 or 3 heteroatoms selected from N, O and S. In one embodiment, $R^3$ is a group of formula (ii) and Ring A is selected from aryl, 5-10 membered heterocycle having 1, 2 or 3 heteroatoms selected from N, O and S and 5-10 membered heteroaryl having 1, 2 or 3 heteroatoms selected from N, O and S. In one particular embodiment, $R^3$ is a group of formula (ii) and Ring A is selected from aryl and 5-10 membered heteroaryl having 1, 2 or 3 heteroatoms selected from N, O and S.

In one embodiment, $R^3$ is a group of formula (ii) and Ring A is selected from cycloalkyl, tetrahydropyran, tetrahydrofuran, morpholine, piperidine, phenyl, naphthyl, thiophene, furan, pyrrole, pyrrolidine, pyrrolidinone, imidazole, benzofuran, benzimidazole, pyridyl,

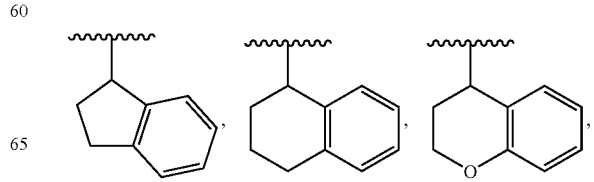

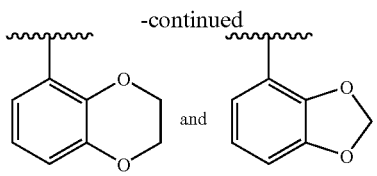

and or any subset thereof. In one particular embodiment, Ring A is phenyl. In one particular embodiment Ring A is pyridyl.

Specific examples of the group —$Y^1$—$(R^2)_m$—$R^3$ in the compounds of formula (I) are selected from:

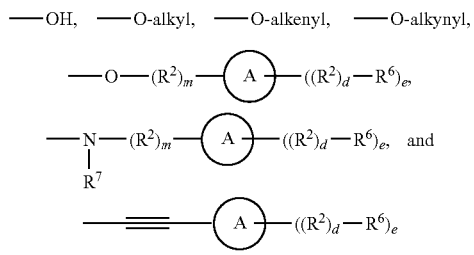

or any subset thereof.

In one embodiment, the group —$Y^1$—$(R^2)_m$—$R^3$ is:

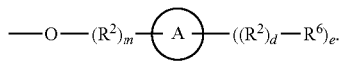

In one embodiment, the group —$Y^1$—$(R^2)_m$—$R^3$ is:

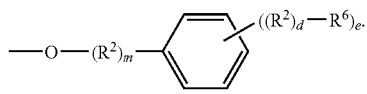

In one particular embodiment, the group —$Y^1$—$(R^2)_m$—$R^3$ is:

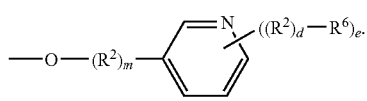

In one particular embodiment, group —$Y^1$—$(R^2)_m$—$R^3$ is:

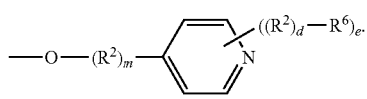

In one embodiment the compounds of formula (I) are defined wherein $R^3$ is a group of formula (ii) and d is 0 or 1. In a particular embodiment, wherein $R^3$ is a group of formula (ii), d is 1 and $(R^2)_d$ is $C_{1-3}$alkylene. In one embodiment, d is 0.

In one embodiment, wherein the compounds of formula (I) are defined wherein $R^3$ is a group of formula (ii), e is 0, 1, 2 or 3. In one particular embodiment, e is 0 or 1. In one embodiment, e is 1. In one embodiment, e is 2.

In one embodiment, wherein the compounds of formula (I) are defined wherein $R^3$ is a group of formula (ii), each $R^6$ is the same or different and is independently selected from H, halo, alkyl, alkenyl, alkynyl, cycloalkyl, cycloalkenyl, Ph, Het, —CH(OH)—$R^2$—OH, —C(O)$R^7$, —CO$_2R^7$, —CO$_2$—$R_2$-Ph, —CO$_2$—$R^2$-Het, —C(O)NR$^7R^8$, —C(O)N(R$^7$)C(O)R$^7$, —C(O)N(R$^7$)CO$_2R^7$, —C(O)N(R$^7$)C(O)NR$^7R^8$, —C(O)N(R$^7$)S(O)$_2R^7$, —C(S)R$^7$, —C(S)NR$^7R^8$, —C(=NR$^7$)R$^8$, —C(=NR$^7$)NR$^7R^8$, —CR$^7$=N—OR$^8$, =O, —OR$^7$, —OC(O)R$^7$, —OC(O)Ph, —OC(O)Het, —C(O)NR$^7R^8$, —O—R$^2$—S(O)$_2R^7$, —S(O)$_jR^7$, —S(O)$_2$NR$^7R^8$, —S(O)$_1$Ph, —S(O)$_2$Het, —NR$^7R^8$, —N(R$^7$)C(O)R$^8$, —N(R$^7$)CO$_2R^8$, —N(R$^7$)—R$^2$—CO$_2R^8$, —N(R$^7$)C(O)NR$^7R^8$, —N(R$^7$)—R$^2$—C(O)NR$^7R^8$, —N(R$^7$)C(O)Ph, —N(R$^7$)C(O)Het, —N(R$^7$)Ph, —N(R$^7$)Het, —N(R$^7$)C(O)NR$^7$—R$^2$—NR$^7R^8$, —N(R$^7$)C(O)N(R$^7$)Ph, —N(R$^7$)C(O)N(R$^7$)Het, —N(R$^7$)C(O)N(R$^7$)—R$^2$-Het, —N(R$^7$)S(O)$_2R^8$, —N(R$^7$)—R$^2$—S(O)$_2R^8$, —NO$_2$, —CN and —N$_3$, or any subset thereof. In one particular embodiment, $R^3$ is a group of formula (ii) and each $R^6$ is the same or different and is independently selected from H, halo, alkyl, alkenyl, alkynyl, cycloalkyl, —OR$^7$, —S(O)$_jR^7$, —S(O)$_2$NR$^7R^8$, —NR$^7R^8$, —N(R$^7$)S(O)$_2R^8$, —NO$_2$ and —CN, or any subset thereof. In one particular embodiment, $R^3$ is a group of formula (ii) and each $R^6$ is the same or different and is independently selected from H, halo, alkyl, —OR$^7$, —S(O)$_jR^7$, —S(O)$_2$NR$^7R^8$ and —NO$_2$, or any subset thereof.

More specifically, in one embodiment wherein $R^3$ is a group of formula (ii), each $R^6$ is the same or different and is independently selected from H, F, Cl, Br, I, methyl, trifluoromethyl, ethyl, propyl, isopropyl, cyclopropyl, iso-butyl, t-butyl, ethenyl, propenyl, acetylene, O-methyl, O-difluoromethyl, O-trifluoromethyl, O-ethyl, O-propyl, O-isopropyl, O-cyclopropyl, —SO$_2$-methyl, —SO$_2$NH$_2$, —NH$_2$, —NH(alkyl), —N(alkyl)alkyl, —NH(cyclopropyl), —NHSO$_2$-methyl, —NO$_2$, and —CN, or any subset thereof.

In one embodiment, the group —$Y^1$—$(R^2)_m$—$R^3$ is defined such that when $Y^1$ is —O—, —S— or —NR$^7$— and m is 0, then $R^3$ is not halo, —CO$_2R^7$, —C(S)R$^7$, —C(S)NR$^7R^8$, —C(=NR$^7$)R$^8$, —C(=NR$^7$)NR$^7R^8$, —CR$^7$=N—OR$^7$, —OR$^7$, —S(O)$_2$NR$^7R^8$, —NR$^7R^8$, —N(R$^7$)C(O)R$^8$, —N(R$^7$)S(O)$_2R^8$, —NO$_2$, —CN or —N$_3$. In one embodiment, the group —$Y^1$—$(R^2)_m$—$R^3$ is defined such that when $Y^1$ is —O—, —S— or —NR$^7$— and m is 0, then $R^3$ is not halo, —C(O)R$^7$, —C(O)NR$^7R^8$, —CO$_2R^7$, —C(S)R$^7$, —C(S)NR$^7R^8$, —C(=NR$^7$)R$^8$, —C(=NR$^7$)NR$^7R^8$, —CR$^7$=N—OR$^7$, —OR$^7$, —S(O)$_jR^7$, —S(O)$_2$NR$^7R^8$, —NR$^7R^8$, —N(R$^7$)C(O)R$^8$, —N(R$^7$)S(O)$_2R^8$, —NO$_2$, —CN or —N$_3$.

In one embodiment, n is 0, 1 or 2, or any subset thereof. In one particular embodiment, n is 0, and thus the benzimidazole ring is unsubstituted at positions C-4, C-5, C-6 and C-7. In on embodiment, n is 1. In one embodiment n is 2.

Q is a group of formula —$(R^2)_a$—$(Y^2)_b$—$(R^2)_c$—$R^4$. Q may be located at any of C-4, C-5, C-6 and/or C-7 of the benzimidazole ring. In one embodiment, n is 1 and Q is at C-5. In one embodiment, n is 1 and Q is at C-6. In one particular embodiment, n is 2 and Q is at C-5 and C-6.

In the foregoing formula, a, b and c are the same or different and are each independently 0 or 1.

In one embodiment, a is 0; thus the group $(R^2)_a$ is not present. In the embodiment wherein a is 1, $(R^2)_a$ is typically alkylene or alkenylene, more particularly alkylene. In one particular embodiment, when Q is defined where a is 1, $(R^2)_a$ is $C_{1-3}$alkylene.

In one embodiment, the compounds of formula (I) are defined wherein b is 0. In another embodiment, Q in the compounds of formula (I) is defined where b is 1; thus $Y^2$ is present. $Y^2$ is selected from —O—, —S(O)$_f$—, —N(R$^7$)—, —C(O)—, —OC(O)—, —CO$_2$—, —C(O)N(R$^7$)—, —C(O)N(R$^7$)S(O)$_2$—, —OC(O)N(R$^7$)—, —OS(O)$_2$—, —S(O)$_2$N(R$^7$)—, —S(O)$_2$N(R$^7$)C(O)—, —N(R$^7$)S(O)$_2$—, —N(R$^7$)C(O)—, —N(R$^7$)CO$_2$— and —N(R$^7$)C(O)N(R$^7$)—. In one embodiment wherein b is 1, $Y^2$ is selected from —O—, —S(O)$_f$—, —N(R$^7$)—, —C(O)—, —OC(O)—, —CO$_2$—, —C(O)N(R$^7$)—, —OS(O)$_2$—, —N(R$^7$)S(O)$_2$—, —N(R$^7$)C(O)—, —N(R$^7$)CO$_2$— and —N(R$^7$)C(O)N(R$^7$)—, or any subset thereof. In another particular embodiment, b is 1 and $Y^2$ is selected from —O—, —S(O)$_f$—, —N(R$^7$)—, —CO$_2$—, —C(O)N(R$^7$)—, —N(R$^7$)S(O)$_2$—, and —N(R$^7$)C(O)—, —N(R$^7$)CO$_2$— and —N(R$^7$)C(O)N(R$^7$)—, or any subset thereof. In one particular embodiment, Q is defined wherein b is 1 and $Y^2$ is selected from —O—, —S(O)$_f$—, —N(R$^7$)—, —CO$_2$— and —C(O)N(R$^7$)—, or any subset thereof. In one particular embodiment, Q is defined wherein b is 1 and $Y^2$ is selected from —O—, —S(O)$_f$— and —N(R$^7$)—, or any subset thereof. In one particular embodiment, Q is defined wherein b is 1 and $Y^2$ is —O—. In one particular embodiment, Q is defined wherein b is 1 and $Y^2$ is —S(O)$_f$—, wherein f is 2. In another particular embodiment, b is 1 and $Y^2$ is —N(R$^7$)— and R$^7$ is H or alkyl, more particularly H. In another particular embodiment, b is 1 and $Y^2$ is —CO$_2$—. In another particular embodiment, b is 1 and $Y^2$ is —C(O)N(R$^7$)—. In another particular embodiment, b is 1 and $Y^2$ is —N(R$^7$)C(O)— and R$^7$ is H or alkyl. In another particular embodiment, b is 1 and $Y^2$ is —N(R$^7$)SO$_2$— and R$^7$ is H or alkyl, The variable c in the formula Q can be 0 or 1. In one embodiment, c is 1. In one such embodiment (R$^2$)$_c$ is alkylene or alkenylene, more particularly alkylene. In one particular embodiment where c is 1, (R$^2$)$_c$ is $C_{1-3}$alkylene.

Consistent with the definition of b, $Y^2$ and c, the group R$^4$ may be selected from H, halo, alkyl, alkenyl, alkynyl, —C(O)R$^7$, —C(O)NR$^7$R$^8$, —CO$_2$R$^7$, —C(S)R$^7$, —C(S)NR$^7$R$^8$, —C(=NR$^7$)R$^8$, —C(=NR$^7$)NR$^7$R$^8$, —CR=N—OR$^7$, —OR$^7$, —S(O)$_f$R$^7$, —S(O)$_2$NR$^7$R$^8$, —NR$^7$R$^8$, —N(R$^7$)C(O)R$^8$, —N(R$^7$)S(O)$_2$R$^8$, —NO$_2$, —CN, —N$_3$ and a group of formula (ii):

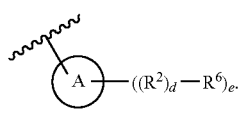

ii

In one embodiment, R$^4$ in the definition of Q is selected from H, halo, alkyl, alkenyl, alkynyl, —C(O)NR$^7$R$^8$, —OR$^7$, —S(O)$_f$R$^7$, —S(O)$_2$NR$^7$R$^8$, —NR$^7$R$^8$, —N(R$^7$)C(O)R$^8$, —N(R$^7$)S(O)$_2$R$^8$, —NO$_2$, —CN, —N$_3$ and a group of formula (ii), or any subset thereof. In one particular embodiment, R$^4$ is selected from H, halo, alkyl, —OR$^7$, —S(O)$_f$R$^7$, —S(O)$_2$NR$^7$R$^8$, —NR$^7$R$^8$, and a group of formula (ii), or any subset thereof. In one embodiment, R$^4$ is selected from H, halo, alkyl, —OR$^7$, —NR$^7$R$^8$, and a group of formula (ii), or any subset thereof.

In one particular embodiment, R$^4$ is a group of formula (ii). In the embodiment, wherein R$^4$ is a group of formula (ii), Ring A is selected from $C_{5-10}$cycloalkyl, $C_{5-10}$cycloalkenyl, aryl, 5-10 membered heterocycle having 1, 2 or 3 heteroatoms selected from N, O and S and 5-10 membered heteroaryl having 1, 2 or 3 heteroatoms selected from N, O and S. In one embodiment, wherein R$^4$ is a group of formula (ii), Ring A is selected from $C_{5-6}$cycloalkyl, $C_{5-6}$cycloalkenyl, aryl, 5-10 membered heterocycle having 1, 2 or 3 heteroatoms selected from N, O and S and 5-10 membered heteroaryl having 1, 2 or 3 heteroatoms selected from N, O and S. In Q, Ring A may be bonded to the R$^2$,Y$^2$ (when c is 0) or the benzimidazole (when a, b and c are 0) through any suitable carbon or heteroatom. In one embodiment, Q is defined wherein R$^4$ is a group of formula (ii) and Ring A is selected from aryl, 5-10 membered heterocycle having 1, 2 or 3 heteroatoms selected from N, O and S and 5-10 membered heteroaryl having 1, 2 or 3 heteroatoms selected from N, O and S. In one particular embodiment, Q is defined wherein R$^4$ is a group of formula (ii) and Ring A is selected from aryl and 5-10 membered heterocycle having 1, 2 or 3 heteroatoms selected from N, O and S.

In one embodiment, Q is defined wherein R$^4$ is a group of formula (ii) and Ring A is selected from cycloalkyl, oxetane, oxazole, thiazole, morpholine, piperidine, piperazine, phenyl, naphthyl, thiophene, furan, pyrrolidine, pyrrolidinone, imidazole, triazole, imidazolidinone, benzofuran, benzodioxolane, benzimidazole, pyrimidyl and pyridyl, or any subset thereof. In one particular embodiment, Ring A is selected from morpholine, piperidine, piperazine, phenyl, pyrrolidinone, imidazolidinone and pyrrolidine, or any subset thereof.

More specifically, in one embodiment, each R$^4$ is the same or different and is independently selected from H, F, Cl, Br, I, methyl, trifluoromethyl, ethyl, propyl, isopropyl, cyclopropyl, iso-butyl, t-butyl, ethenyl, propenyl, acetylene, O-methyl, O-trifluoromethyl, O-ethyl, O-propyl, O-isopropyl, O-cyclopropyl, —SO$_2$-methyl, —SO$_2$NH$_2$, —NH$_2$, —NH(alkyl), —N(alkyl)alkyl, —NH(cyclopropyl), —NHC(O)-methyl, —NHC(O)NH$_2$, —NHSO$_2$-methyl, morpholino and piperizinyl, or any subset thereof.

Particular, more specific, examples of groups defining Q in the compounds of formula (I) are selected from the group consisting of:

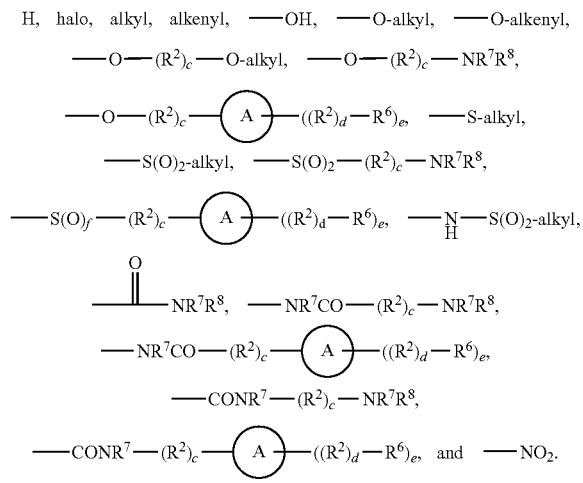

In one embodiment, Q is alkyl, particularly $C_{1-3}$alkyl (including $C_{1-3}$haloalkyl) In one embodiment, Q is —O-alkyl (including O—$C_{1-3}$haloalkyl). In one embodiment, Q is halo.

In one embodiment the compounds of formula (I) are defined wherein R$^4$ is a group of formula (ii) and d is 0 or 1. In a particular embodiment, wherein R$^4$ is a group of formula (ii) and d is 1, (R$^2$)$_d$ is $C_{1-3}$alkylene. In one embodiment, d is 0.

In one embodiment, wherein the compounds of formula (I) are defined wherein $R^4$ is a group of formula (ii), e is 0, 1, 2 or 3. In one particular embodiment, e is 0 or 1. In one embodiment, e is 0. In one embodiment, e is 1. In one embodiment, e is 2.

In one embodiment, wherein the compounds of formula (I) are defined wherein $R^4$ is a group of formula (ii), each $R^6$ is the same or different and is independently selected from H, halo, alkyl, alkenyl, alkynyl, Het, —C(O)$R^7$, —CO$_2R^7$, —C(O)N$R^7R^8$, =O, —O$R^7$, —S(O)$_fR^7$, —S(O)$_2$N$R^7R^8$, —N$R^7R^8$ and —N($R^7$)S(O)$_2R^8$, or any subset thereof. In one particular embodiment, each $R^6$ is the same or different and is independently selected from H, halo, alkyl, =O, —O$R^7$, —S(O)$_fR^7$, —S(O)$_2$N$R^7R^8$ and —N$R^7R^8$, or any subset thereof.

More specifically, in one embodiment, each $R^6$ is the same or different and is independently selected from H, methyl, ethyl, propyl, isopropyl, iso-butyl, t-butyl, ethenyl, propenyl, cyclopropyl, pyrimidyl, —C(O)-alkyl, —CO$_2$-alkyl, —C(O)NH$_2$, acetylene, oxo, O-methyl, O-ethyl, O-propyl, O-isopropyl, O-cyclopropyl, —SO$_2$-methyl, —SO$_2$NH$_2$, —NH$_2$, —NH(alkyl), —N(alkyl)alkyl, —NH(cyclopropyl) and —NHSO$_2$-methyl, or any subset thereof.

In another embodiment of the present invention, two adjacent Q groups are selected from alkyl, alkenyl, —O$R^7$, —S(O)$_fR^7$ and —N$R^7R^8$ and together with the carbon atoms to which they are bound, they form a $C_{5-6}$cycloalkyl, $C_{5-6}$cycloalkenyl, phenyl, 5-7 membered heterocycle having 1 or 2 heteroatoms selected from N, O and S, or 5-6 membered heteroaryl having 1 or 2 heteroatoms selected from N, O and S. By "two adjacent Q groups" is meant that two Q groups are bonded to adjacent carbon atoms (e.g., C-4 and C-5). For example, in one embodiment two adjacent Q groups are —O$R^7$ and together with the atoms to which they are bonded, they form a heterocyclic group such as:

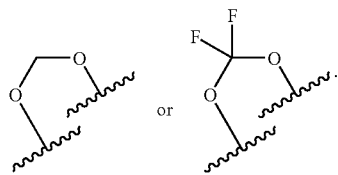

In another embodiment, two adjacent Q groups are alkyl and together with the atoms to which they are bonded, they form a cycloalkyl group such as:

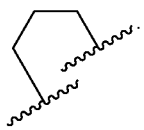

In another embodiment two adjacent Q groups are defined as —O$R^7$ and —N$R^7R^8$ respectively and together with the atoms to which they are bonded, they form a heterocyclic group such as:

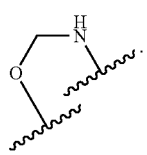

From these examples, additional embodiments can be readily ascertained by those skilled in the art. Preferably the compounds of formula (I) are defined wherein when n is 2, two adjacent Q groups together with the atoms to which they are bonded do not form a $C_{5-6}$cycloalkyl, $C_{5-6}$cycloalkenyl, phenyl, 5-7 membered heterocycle having 1 or 2 heteroatoms selected from N, O and S, or 5-6 membered heteroaryl having 1 or 2 heteroatoms selected from N, O and S.

In one embodiment, when Q is defined where b is 1 and c is 0, then $R^4$ is not halo, —C(O)$R^7$, —C(O)N$R^7R^8$, —CO$_2R^7$, —C(S)$R^7$, —C(S)N$R^7R^8$, —C(=N$R^7$)$R^8$, —C(=N$R^7$)N$R^7R^8$, —C$R^7$=N—O$R^7$, —O$R^7$, —S(O)$_fR^7$, —S(O)$_2$N$R^7R^8$, —N$R^7R^8$, —N($R^7$)C(O)$R^8$, —N($R^7$)S(O)$_2R^8$, —NO$_2$, —CN or —N$_3$.

In one embodiment, $R^5$ is selected from H, halo, alkyl, —N$R^7R^8$ and —S(O)$_fR^7$, or any subset thereof. In another embodiment, $R^5$ is selected from H, halo, alkyl and —N$R^7R^8$, or any subset thereof. In one particular embodiment, $R^5$ is H. In one particular embodiment, $R^5$ is —NH$_2$.

More specifically, in one embodiment, $R^5$ is selected from H, F, Cl, Br, I, methyl, trifluoromethyl, ethyl, propyl, isopropyl, —S-methyl, —SO$_2$-methyl and —NH$_2$, or any subset thereof.

The present invention also provides compounds of formula (Ia):

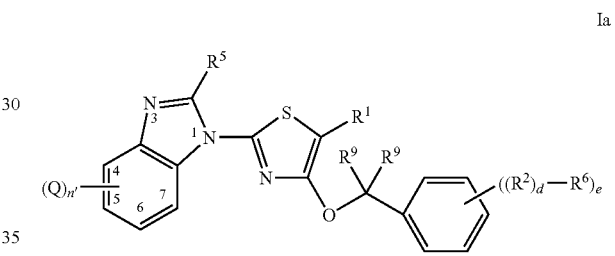

wherein:
n' is 0, 1 or 2;
each $R^9$ is the same or different and is selected from H, halo and alkyl; and
all other variables are as defined above, and pharmaceutically acceptable salts, solvates and physiologically functional derivatives thereof.

The present invention also provides compounds of formula (Ib):

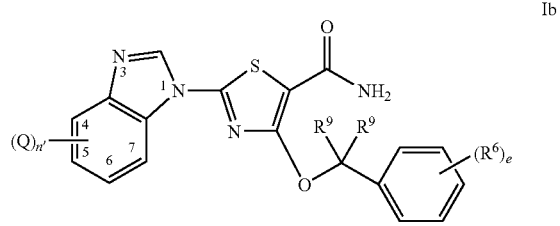

wherein
n' is 0, 1 or 2;
Q is selected from H, halo, $C_{1-3}$alkyl (including $C_{1-3}$haloalkyl), and O—$C_{1-3}$alkyl (including O—$C_{1-3}$haloalkyl);
$R^6$ is selected from H, halo, $C_{1-3}$alkyl (including $C_{1-3}$haloalkyl), and O—$C_{1-3}$alkyl (including O—$C_{1-3}$haloalkyl)
each $R^9$ is the same or different and is selected from H, halo and alkyl; and all other variables are as defined above, and pharmaceutically acceptable salts, solvates and physiologically functional derivatives thereof.

It is to be understood that the present invention includes all combinations and subsets of the particular groups defined hereinabove.

Specific compounds of formula (I) include but are not limited to those compounds described in the Example section that follows. Some particular compounds of formula (I) include but are not limited to:

2-(1H-Benzimidazol-1-yl)-4-({[2-(trifluoromethyl)phenyl]methyl}-oxy)-1,3-thiazole-5-carboxamide;

2-(6-Chloro-1H-benzimidazol-1-yl)-4-({[2-(trifluoromethyl)phenyl]methyl}oxy)-1,3-thiazole-5-carboxamide;

2-(5-chloro-1H-benzimidazol-1-yl)-4-({[2-(trifluoromethyl)phenyl]methyl}oxy)-1,3-thiazole-5-carboxamide;

2-(6-Methoxy-1H-benzimidazol-1-yl)-4-({[2-(trifluoromethyl)phenyl]methyl}oxy)-1,3-thiazole-5-carboxamide;

2-(5-methoxy-1H-benzimidazol-1-yl)-4-({[2-(trifluoromethyl)phenyl]methyl}oxy)-1,3-thiazole-5-carboxamide;

2-(6-Fluoro-1H-benzimidazol-1-yl)-4-({f[2-(trifluoromethyl)phenyl]methyl}oxy)-1,3-thiazole-5-carboxamide;

2-(5,6-Dimethyl-1H-benzimidazol-1-yl)-4-({[2-(trifluoromethyl)phenyl]methyl}oxy)-1,3-thiazole-5-carboxamide;

2-[5,6-Bis(methyloxy)-1H-benzimidazol-1-yl]-4-({[2-(trifluoromethyl)phenyl]-methyl}oxy)-1,3-thiazole-5-carboxamide, and pharmaceutically acceptable salts, solvates and physiologically functional derivatives thereof.

It will be appreciated by those skilled in the art that the compounds of the present invention may also be utilized in the form of a pharmaceutically acceptable salt or solvate or physiologically functional derivative thereof. The pharmaceutically acceptable salts of the compounds of formula (I) include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic(mesylate), naphthalene-2-sulfonic, benzenesulfonic hydroxynaphthoic, hydroiodic, malic, steroic, tannic and the like.

Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

The term "solvate" as used herein refers to a complex of variable stoichiometry formed by a solute (a compound of formula (I)) and a solvent. Solvents, by way of example, include water, methanol, ethanol, or acetic acid.

The term "physiologically functional derivative" as used herein refers to any pharmaceutically acceptable derivative of a compound of the present invention, for example, an ester or an amide of a compound of formula (I), which upon administration to an animal, particularly a mammal, such as a human, is capable of providing (directly or indirectly) a compound of the present invention or an active metabolite thereof. See, for example, Burger's Medicinal Chemistry And Drug Discovery, 5th Edition, Vol 1: Principles And Practice.

Processes for preparing pharmaceutically acceptable salts, solvates and physiologically functional derivatives of the compounds of formula (I) are conventional in the art. See, e.g., Burger's Medicinal Chemistry And Drug Discovery 5th Edition, Vol 1: Principles And Practice.

As will be apparent to those skilled in the art, in the processes described below for the preparation of compounds of formula (I), certain intermediates, may be in the form of pharmaceutically acceptable salts, solvates or physiologically functional derivatives of the compound. Those terms as applied to any intermediate employed in the process of preparing compounds of formula (I) have the same meanings as noted above with respect to compounds of formula (I). Processes for preparing pharmaceutically acceptable salts, solvates and physiologically functional derivatives of such intermediates are known in the art and are analogous to the process for preparing pharmaceutically acceptable salts, solvates and physiologically functional derivatives of the compounds of formula (I).

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Certain compounds of formula (I) may be prepared as a mixture of regioisomers. The present invention covers both the mixture of regioisomers as well as the individual compounds. Likewise, it is understood that compounds of formula (I) may exist in tautomeric forms other than that shown in the formula and these are also included within the scope of the present invention. In one particular embodiment of the present invention, the chiral compounds defined wherein m is 1 exhibit the following stereochemistry:

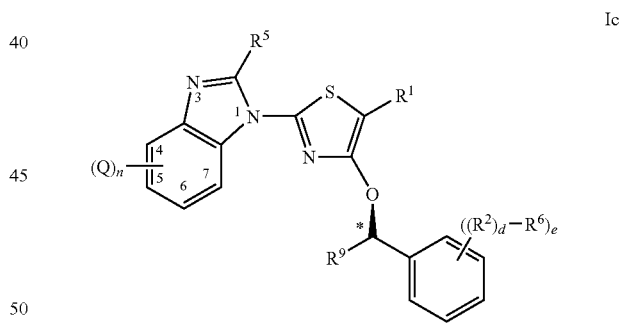

Ic

The compounds of the present invention are inhibitors of PLK. By PLK inhibitor is meant a compound which exhibits $pIC_{50}$ greater than 4 in the PLK Inhibition assay described below in the examples or an $IC_{50}$ less than 100 μM in the Methylene Blue Growth Inhibition assay described below in the examples; more particularly a PLK inhibitor is a compound which exhibits a $pIC_{50}$ greater than 5 or an $IC_{50}$ less than 10 μM using the methods described in the examples below.

The present invention further provides compounds of formula (I) for use in medical therapy in an animal, e.g. a mammal such as a human. In particular, the present invention provides compounds of formula (I) for use in the treatment of a condition mediated by PLK. The present invention also provides compounds of formula (I) for use in the treatment of a neoplasm susceptible to PLK. The present invention provides compounds of formula (I) for use in treating a PLK-mediated condition characterized by inappropriate cellular proliferation. The present invention also provides compounds of formula (I) for use in inhibiting proliferation of a cell, via PLK. The present invention also provides compounds of formula (I) for use in inhibiting mitosis in a cell, via PLK.

The present invention provides methods for the treatment of several conditions or diseases, all of which comprise the step of administering a therapeutically effective amount of a compound of formula (I). As used herein, the term "treatment" refers to alleviating the specified condition, eliminating or reducing the symptoms of the condition, slowing or eliminating the progression of the condition and preventing or delaying the reoccurrence of the condition in a previously afflicted subject.

As used herein, the term "therapeutically effective amount" means an amount of a compound of formula (I) which is sufficient, in the subject to which it is administered, to elicit the biological or medical response of a cell culture, tissue, system, animal (including human) that is being sought, for instance, by a researcher or clinician. For example, a therapeutically effective amount of a compound of formula (I) for the treatment of a condition mediated by PLK is an amount sufficient to treat the PLK-mediated condition in the subject. Similarly, a therapeutically effective amount of a compound of formula (I) for the treatment of a neoplasm susceptible to PLK (i.e., a susceptible neoplasm) is an amount sufficient to treat the susceptible neoplasm in the subject. In one embodiment of the present invention, the therapeutically effective amount of a compound of formula (I) is an amount sufficient to inhibit cell mitosis. In one embodiment of the present invention, a therapeutically effective amount of a compound of formula (I) is an amount sufficient to regulate, modulate, bind or inhibit PLK.

The precise therapeutically effective amount of the compounds of formula (I) will depend on a number of factors including, but not limited to, the age and weight of the subject being treated, the precise disorder requiring treatment and its severity, the nature of the formulation, and the route of administration, and will ultimately be at the discretion of the attendant physician or veterinarian. Typically, the compound of formula (I) will be given for treatment in the range of 0.1 to 200 mg/kg body weight of recipient (animal) per day and more usually in the range of 1 to 100 mg/kg body weight per day. Acceptable daily dosages, may be from about 0.1 to about 2000 mg/day, and preferably from about 0.1 to about 100 mg/day.

As one aspect, the present invention provides methods of regulating, modulating, binding, or inhibiting PLK for the treatment of conditions mediated by PLK. "Regulating, modulating, binding or inhibiting PLK" refers to regulating, modulating, binding or inhibiting PLK activity, as well as regulating, modulating, binding or inhibiting overexpression of PLK. Such conditions include certain neoplasms (including cancers and tumors) which are associated with PLK and conditions characterized by inappropriate cellular proliferation which are associated with PLK.

The present invention provides a method for treating a condition mediated by PLK in an animal such as a mammal (e.g., a human), which method comprises administering to the animal a therapeutically effective amount of the compound of formula (I). Conditions which are mediated by PLK and techniques for determining whether a given condition is mediated by PLK are known in the art. See, e.g., Takahashi, T. et al., Cancer Science, 94: 148-52. Wolf, G. et al., Oncogene, 14: 543-9). Such conditions include but are not limited to neoplasms and conditions characterized by inappropriate cellular proliferation.

The present invention also provides a method for treating a neoplasm (cancer or tumor) that is susceptible to PLK in an animal such as a mammal (e.g., a human), which method comprises administering to the animal a therapeutically effective amount of the compound of formula (I). "Susceptible neoplasm" as used herein refers to neoplasms which are susceptible to treatment with a PLK regulator, modulator, binder or inhibitor. In one embodiment, a susceptible neoplasm refers to neoplasms which are susceptible to treatment with a PLK inhibitor. Neoplasms which have been associated with PLK and are therefor susceptible to PLK are known in the art, and include both primary and metastatic tumors and cancers. For example, susceptible neoplasms within the scope of the present invention include but are not limited to breast cancer, colon cancer, lung cancer (including small cell lung cancer and non-small cell lung cancer), prostate cancer, lymphoma, leukemia, endometrial cancer, melanoma, ovarian cancer, pancreatic cancer, squamous carcinoma, carcinoma of the head and neck, and esophageal carcinoma. The compounds of formula (I) can be used alone in the treatment of such susceptible neoplasms or can be used to provide additive or synergistic effects with certain existing chemotherapies, and/or be used to restore effectiveness of certain existing chemotherapies and radiation.

The present invention also provides a method for treating a PLK-mediated condition characterized by inappropriate cellular proliferation. By PLK-mediated mediated condition" is meant a condition mediated by PLK as described above. By "inappropriate cellular proliferation" is meant cellular proliferation resulting from inappropriate cell growth, cellular proliferation resulting from excessive cell division, cellular proliferation resulting from cell division at an accelerated rate, cellular proliferation resulting from inappropriate cell survival, and/or cellular proliferation in a normal cell occurring at a normal rate, which is nevertheless undesired. Conditions characterized by inappropriate cellular proliferation include but are not limited to neoplasms, blood vessel proliferative disorders, fibrotic disorders, mesangial cell proliferative disorders and metabolic diseases. Blood vessel proliferative disorders include arthritis and restenosis. Fibrotic disorders include hepatic cirrhosis and atherosclerosis. Mesangial cell proliferative disorders include glomerulonephritis, malignant nephrosclerosis, thrombotic microangiopathy syndromes, organ transplant rejection and glomerulopathies. Metabolic disorders include psoriasis, chronic wound healing, inflammation and neurodegenerative diseases. Osteoarthritis and other osteoclast proliferation dependent diseases of excess bone resorbtion are examples of conditions characterized by inappropriate cellular proliferation in which the cellular proliferation occurs in normal cells at a normal rate, but is nevertheless undesired.

The present invention also provides a method for inhibiting proliferation of a cell with a PLK inhibitor, which method comprises contacting the cell with an amount of a compound of formula (I) sufficient to inhibit proliferation of the cell, wherein the compound is a PLK inhibitor. In one particular embodiment, the cell is a neoplastic cell. In one particular embodiment, the cell is an inappropriately proliferative cell. The term "inappropriately proliferative cell" as used herein refers to cells that grow inappropriately (abnormally), cells that divide excessively or at an accelerated rate, cells that inappropriately (abnormally) survive and/or normal cells that proliferate at a normal rate but for which proliferation is undesired. Neoplastic cells (including cancer cells) are an example of inappropriately proliferative cells but are not the only inappropriately proliferative cells.

PLK is essential for cellular mitosis and accordingly, the compounds of formula (I) are effective for inhibiting mitosis via PLK. "Inhibiting mitosis" refers to inhibiting the entry into the M phase of the cell cycle, inhibiting the normal progression of the M phase of the cell cycle once M phase has been entered and inhibiting the normal exit from the M phase of the cell cycle. Thus, the compounds of the present invention may inhibit mitosis through PLK by inhibiting the cell's entry into mitosis, by inhibiting the cell's progression through mitosis or by inhibiting the cell's exit from mitosis. As one aspect, the present invention provides a method for inhibiting mitosis in a cell, which method comprises administering to the cell an amount of a compound of formula (I) sufficient to inhibit mitosis, wherein the compound inhibits PLK. In one particular embodiment, the cell is a neoplastic cell. In one particular embodiment, the cell is an inappropriately proliferative cell.

The present invention also provides the use of a compound of formula (I) for the preparation of a medicament for the treatment of condition mediated by PLK in an animal, such as a mammal (e.g., a human). The present invention further provides the use of a compound of formula (I) for the preparation of a medicament for the treatment of a neoplasm susceptible to PLK in an animal. The present invention further provides the use of a compound of formula (I) for the preparation of a medicament for the treatment of a PLK-mediated condition characterized by inappropriate cellular proliferation. The present invention further provides the use of a compound of formula (I) for the preparation of a medicament for inhibiting proliferation of a cell, via inhibiting PLK. The present invention further provides the use of a compound of formula (I) for the preparation of a medicament for inhibiting mitosis in a cell, via inhibiting PLK.

While it is possible that, for use in therapy, a therapeutically effective amount of a compound of formula (I) may be administered as the raw chemical, it is typically presented as the active ingredient of a pharmaceutical composition or formulation. Accordingly, the invention further provides a pharmaceutical composition comprising a compound of the formula (I). The pharmaceutical composition may further comprise one or more pharmaceutically acceptable carriers, diluents, and/or excipients. The carrier(s), diluent(s) and/or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I) with one or more pharmaceutically acceptable carriers, diluents and/or excipients.

Pharmaceutical formulations may be presented in unit dose form containing a predetermined amount of active ingredient per unit dose. Such a unit may contain a therapeutically effective dose of the compound of formula (I) or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of active ingredient. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I) can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) may also be delivered by the use of monoclonal antibodies as individual carriers to which the compound molecules are coupled. The compounds may also be coupled with soluble polymers as targetable drug carriers. Such polymers can include peptides, polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research*, 3(6):318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

In the above-described methods of treatment and uses, a compound of formula (I) may be employed alone, in combination with one or more other compounds of formula (I) or in combination with other therapeutic agents. In particular, in methods of treating conditions mediated by PLK and methods of treating neoplasms susceptible to PLK, combination with other chemotherapeutic, hormonal and/or antibody agents is envisaged as well as combination with surgical therapy and radiotherapy. The term "chemotherapeutic" as used herein refers to any chemical agent having a therapeutic effect on the subject to which it is administered.

"Chemotherapeutic" agents include but are not limited to anti-neoplastic agents, analgesics and anti-emetics. As used herein, "anti-neoplastic agents" include both cytostatic and cytotoxic agents. Combination therapies according to the present invention thus comprise the administration of at least one compound of formula (I) and the use of at least one other cancer treatment method. In one embodiment, combination therapies according to the present invention comprise the administration of at least one compound of formula (I) and at least one other chemotherapeutic agent. In one particular embodiment, the present invention comprises the administration of at least one compound of formula (I) and at least one anti-neoplastic agent. As an additional aspect, the present invention provides the methods of treatment and uses as described above, which comprise administering a compound of formula (I) together with at least one chemotherapeutic agent. In one particular embodiment, the chemotherapeutic agent is an anti-neoplastic agent. In another embodiment, the present invention provides a pharmaceutical composition as described above further comprising at least one other chemotherapeutic agent, more particularly, the chemotherapeutic agent is an anti-neoplastic agent.

Typically, any chemotherapeutic agent that has activity versus a susceptible neoplasm being treated may be utilized in combination with the compounds of formula (I), provided that the particular agent is clinically compatible with therapy employing a compound of formula (I). Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and antifolate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids. Examples of diterpenoids include, but are not limited to, paclitaxel and its analog docetaxel. Examples of vinca alkaloids include, but are not limited to, vinblastine, vincristine, and vinorelbine.

Platinum coordination complexes are non-phase specific anti-neoplastic agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Alkylating agents are non-phase anti-neoplastic specific agents and strong electrophiles. Typically, alkylating agents form covalent linkages, by alkylation, to DNA through nucleophilic moieties of the DNA molecule such as phosphate, amino, and hydroxyl groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Antibiotic chemotherapeutic agents are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine and thioguanine.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin.

Hormones and hormonal analogues are useful compounds for treating cancers in which there is a relationship between the hormone(s) and growth and/or lack of growth of the cancer. Examples of hormones and hormonal analogues believed to be useful in the treatment of neoplasms include, but are not limited to, adrenocorti-costeroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene and iodoxyfene useful in the treatment of hormone dependent breast carcinoma; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Signal transduction pathway inhibitors are those inhibitors which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes.

Several protein tyrosine kinases catalyse the phosphorylation of specific tyrosyl residues in, various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are sometimes termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr, ErbB2 and ErbB4,), platelet derived growth factor receptor (PDGFr), vascular endothelial growth factor receptor (VEGFR), tyrosine kinase with immunoglobulin-like and epidermal growth factor homology domains (TIE-2), insulin growth factor-I receptor (IGF-I), macrophage colony stimulating factor (cfms), BTK, ckit, cmet, fibroblast growth factor (FGF) receptors, Trk receptors (TrkA, TrkB, and TrkC), ephrin (eph)

receptors, and the RET protooncogene. Several inhibitors of growth factor receptors are under development and include ligand antagonists, antibodies, tyrosine kinase inhibitors, anti-sense oligonucleotides and aptamers. Growth factor receptors and agents that inhibit growth factor receptor function are described, for instance, in Kath, John C., Exp. Opin. Ther. Patents (2000) 10(6):803-818; Shawver et al DDT Vol 2, No. 2 February 1997; and Lofts, F. J. et al, "Growth Factor Receptors as Targets", New Molecular Targets for Cancer Chemotherapy, Ed. Workman, Paul and Kerr, David, CRC Press 1994, London.

Tyrosine kinases, which are not growth factor receptor kinases are termed non-receptor tyrosine kinases. Non-receptor tyrosine kinases useful in the present invention, which are targets or potential targets of anti-neoplastic drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual Review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (Rafk), Mitogen or Extracellular Regulated Kinase (MEKs), and Extracellular Regulated Kinases (ERKs); and Protein kinase C family member blockers including blockers of subtypes of PKCs (alpha, beta, gamma, epsilon, mu, lambda, iota, zeta), IkB kinase family (IKKa, IKKb), PKB family kinases, Akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; and Martinez-Iacaci, L., et al, Int. J. Cancer (2000), 88(1), 44-52.

Inhibitors of Phosphotidyl Inositol-3 Kinase family members including blockers of PI3-kinase, ATM, DNA-PK, and Ku are also useful in combination with the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer Res, (2000) 60(6), 1541-1545.

Also useful in combination with the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC Press 1994, London.

Another group of signal transduction pathway inhibitors useful in combination with the present invention are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block Ras activation in cells containing wild type mutant Ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, Minn. (1998), Current Opinion in Lipidology. 9(2)99-102; and BioChim. Biophys. Acta, (1989) 1423(3):19-30.

As mentioned above, antibodies to receptor kinase ligand binding may also serve as signal transduction inhibitors. This group of signal transduction pathway inhibitors includes the use of humanized antibodies to the extracellular ligand binding domain of receptor tyrosine kinases. For example, Imclone C225 EGFR specific antibody (see Green, M. C. et al, Monoclonal Antibody Therapy for Solid Tumors, Cancer Treat. Rev., (2000), 26(4), 269-286); Herceptin® ErbB2 antibody (see Tyrosine Kinase Signaling in Breast Cancer:ErbB Family Receptor Tyrosine Kinases, Breast Cancer Res., 2000, 2(3), 176-183); and 2CB VEGFR2 specific antibody (see Brekken, R. A. et al, Selective Inhibition of VEGFR2 Activity by a Monoclonal Anti-VEGF Antibody Blocks Tumor Growth in Mice, Cancer Res. (2000) 60, 5117-5124).

Receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Other inhibitors may be used in combination with the compounds of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) may also prove useful in combination with PLK inhibitors.

Agents used in immunotherapeutic regimens may also be useful in combination with the compounds of formula (I).

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al., *J. Clin. Oncol.* 18:1812-1823 (2000); and Kitada S et al., *Antisense Res. Dev.* 4:71-79 (1994).

Cell cycle signaling inhibitors inhibit molecules involved in the control of the cell cycle. Cyclin dependent kinases (CDKs) and their interaction cyclins control progression through the eukaryotic cell cycle. The coordinated activation and inactivation of different cyclin/CDK complexes is necessary for normal progression through the cell cycle. Several inhibitors of cell cycle signaling are under development. For instance, examples of cyclin dependent kinases, including CDK2, CDK4, and CDK6 and inhibitors for the same are described in, for instance, Rosania, et al., *Exp. Opin. Ther. Patents* 10(2):215-230 (2000).

In one embodiment, the methods of the present invention comprise administering to the animal a compound of formula (I) in combination with a signal transduction pathway inhibitor, particularly gefitinib (IRESSA®).

The methods and uses employing these combinations may comprise the administration of the compound of formula (I) and the other chemotherapeutic/anti-neoplastic agent either sequentially in any order or simultaneously in separate or combined pharmaceutical compositions. When combined in the same formulation it will be appreciated that the two compounds must be stable and compatible with each other and the other components of the formulation and may be formulated for administration. When formulated separately they may be provided in any convenient formulation, in such a manner as are known for such compounds in the art.

When a compound of formula (I) is used in combination with a chemotherapeutic agent, the dose of each compound may differ from that when the compound is used alone. Appropriate doses will be readily appreciated by those skilled in the art. The appropriate dose of the compound(s) of formula (I) and the other therapeutically active agent(s) and the relative timings of administration will be selected in order to achieve the desired combined therapeutic effect, and are within the expertise and discretion of the attendant clinician.

Compounds of formula (I) may be conveniently prepared by the methods outlined in Scheme 1 below.

Scheme 1

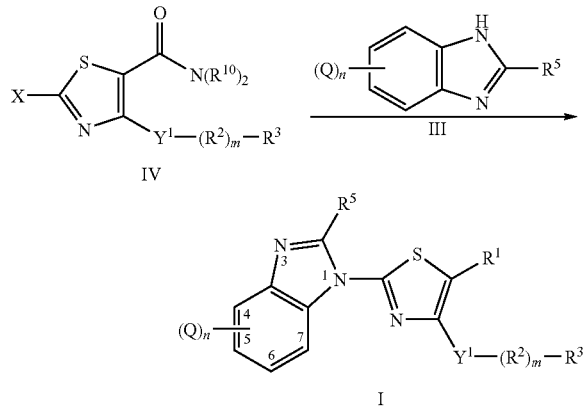

wherein:

X is Cl, Br or I;

each $R^{10}$ is the same or different and is selected from H, alkyl, alkenyl, alkynyl, cycloalkyl and cycloalkenyl; and all other variables are as defined above.

Generally, the process for preparing a compound of formula (I) comprises the steps of:

a) reacting a compound of formula (III) with a compound of formula (IV) to prepare a compound of formula (I);

b) optionally converting the compound of formula (I) to a pharmaceutically acceptable salt, solvate or physiologically functional derivative thereof; and c) optionally converting the compound of formula (I) or a pharmaceutically acceptable salt, solvate or physiologically functional derivative thereof to a different compound of formula (I) or a pharmaceutically acceptable salt, solvate or physiologically functional derivative thereof.

More specifically, the reaction of the compound of formula (III) with the compound of formula (IV) is carried out in the presence of a base at elevated temperature from about 50 to 120° C. The reaction will typically be carried out with equimolar equivalents of the two reactants. Suitable solvents include but are not limited to N,N-dimethylformamide, dimethyl sulfoxide, 1-methyl-2-pyrrolidinone, ethanol, isopropanol, and tetrahydrofuran. Suitable bases include but are not limited to potassium carbonate, sodium carbonate, cesium carbonate, trialkylamines, and potassium tert-butoxide.

The compounds of formula (IV) may be prepared by reacting the compound of formula (V) with an amine of formula $HN(R^{10})_2$

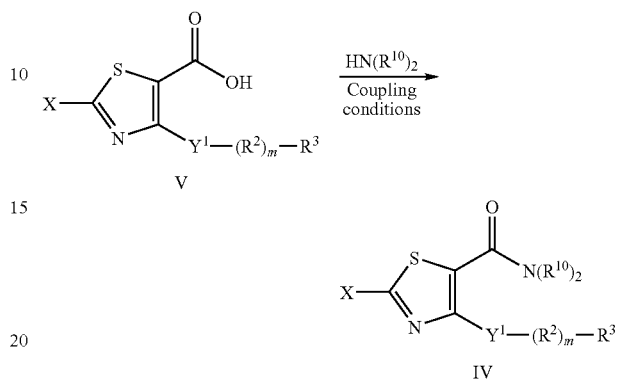

wherein all variables are as defined above.

This reaction may be carried out in an inert solvent using a variety of commercially available coupling reagents. Suitable coupling reagents include but are not limited to N,N-dicyclohexylcarbodiimide, 1-(3-dimethylaminopropyl)-3-ethylcarbodiimide hydrochloride, 1,1'-carbonyldiimidazole, and benzotriazol-1-yloxytris(dimethyl-amino)phosphonium hexafluorophosphate. Other suitable coupling reagents will be readily apparent to those skilled in the art. The carboxylic acid optionally may be converted into the corresponding acid chloride and subsequently treated with the amine of formula $HN(R^{10})_2$. Suitable reagents for the reaction of such acid chlorides include but are not limited to oxalyl chloride, thionyl chloride, and 1-chloro-N,N,2-trimethyl-1-propenylamine. Base may be optionally added to the coupling reaction. The reaction may optionally require heating to a temperature of from about 40 to about 100° C. Suitable bases include but are not limited to trialkylamines, pyridine, and 4-(dimethylamino)pyridine. Examples of suitable solvents for this reaction include but are not limited to dichloromethane, chloroform, benzene, toluene, N,N-dimethylformamide and dichloroethane.

The compound of formula (V) may be prepared by hydrolyzing a compound of formula (VI).

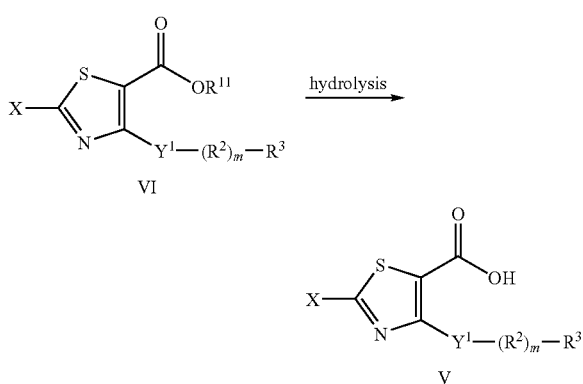

wherein $R^{11}$ is alkyl and all other variables are as defined above.

The reaction is carried out using basic hydrolysis conditions. Examples of suitable reagents include but are not limited to lithium hydroxide and sodium hydroxide. The reaction is run in a biphasic manner with water. Examples of suitable co-solvents include but are not limited to dioxane, tetrahydrofuran, methanol, and ethanol. The reaction may be optionally heated from 40 to 80° C.

The compound of formula (VI) may be prepared by reacting the compound of formula (VII) with a diazonium salt to convert the amine to a halide.

chloric acid or sulfuric acid. The reaction is carried out in the presence of a copper halide salt. Examples of suitable copper halide salts include but are not limited to copper(I) chloride, copper(II) chloride, copper(I) bromide, and copper(II) bromide. The preferred solvent for this reaction is acetonitrile, and the reaction is often run in the presence of water. Other suitable solvents include but are not limited to chloroform, and dichloromethane.

The compound of formula (VII) may be prepared according to Scheme 2 below.

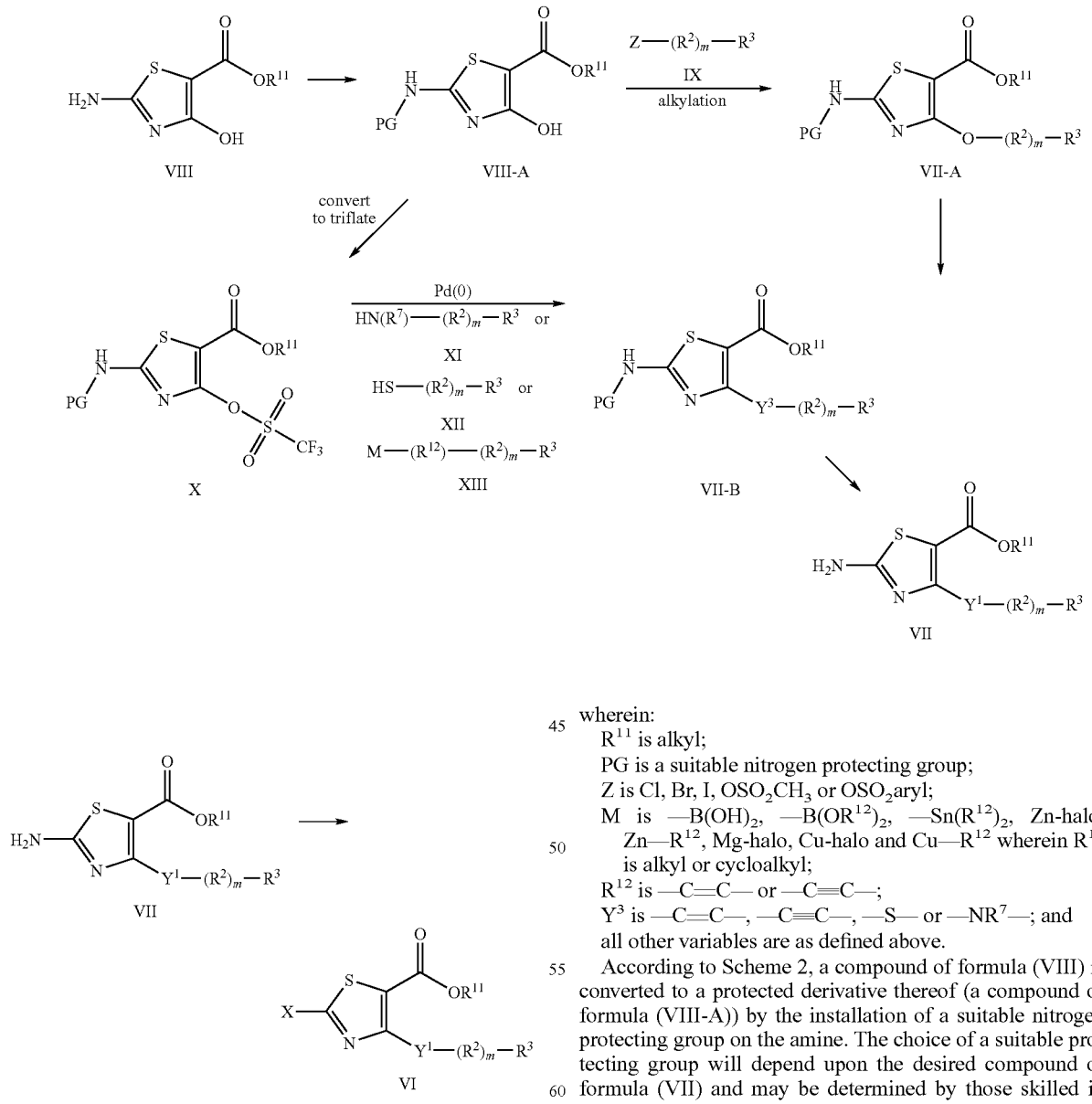

wherein all variables are as defined above.

This reaction is typically carried out using a reagent for formation of the diazonium salt. Suitable reagents for this transformation include but are not limited to t-butyl nitrite or sodium nitrite in the presence of a protic acid, such as hydrowherein:
$R^{11}$ is alkyl;
PG is a suitable nitrogen protecting group;
Z is Cl, Br, I, $OSO_2CH_3$ or $OSO_2$aryl;
M is $-B(OH)_2$, $-B(OR^{12})_2$, $-Sn(R^{12})_2$, Zn-halo, $Zn-R^{12}$, Mg-halo, Cu-halo and $Cu-R^{12}$ wherein $R^{12}$ is alkyl or cycloalkyl;
$R^{12}$ is $-C=C-$ or $-C\equiv C-$;
$Y^3$ is $-C=C-$, $-C\equiv C-$, $-S-$ or $-NR^7-$; and
all other variables are as defined above.

According to Scheme 2, a compound of formula (VIII) is converted to a protected derivative thereof (a compound of formula (VIII-A)) by the installation of a suitable nitrogen protecting group on the amine. The choice of a suitable protecting group will depend upon the desired compound of formula (VII) and may be determined by those skilled in organic synthesis without undue experimentation.

The protected derivative of the compound of formula (VIII) may then be alkylated to obtain a protected derivative of a compound of formula (VII) wherein $Y^1$ is O (i.e., a compound of formula (VII-A). The alkylation reaction may be carried out by reacting the compound of formula (VIII-A) with a compound of Formula (IX).

More specifically, a compound of formula (VII-A) can be prepared by reacting a compound of formula (VIII-A) with a compound of formula (IX). The compounds of formula (IX) are commercially available or can be prepared using conventional knowledge in the art. The reaction may be carried out in an inert solvent, conveniently at room temperature, in the presence of a suitable base. The compound of formula (VIII-A) and the compound of formula (IX) may be present in equimolar amounts; however, a slight excess of the compound of formula (IX) may be employed if desired. Examples of suitable bases for this reaction include but are not limited to, potassium carbonate, sodium carbonate, cesium carbonate, sodium hydride, and potassium hydride. Examples of suitable inert solvents for this reaction include but are not limited to, N,N-dimethylformamide, tetrahydrofuran, dioxane, and 1,2-dimethoxyethane.

Alternatively, if a compound of formula (VII) wherein $Y^1$ is —C=C—, —C≡C—, —S— or —NR$^7$— is desired, such compounds may be obtained by a process comprising the steps of:

a) converting a compound of formula (VIII-A) to a triflate (i.e., a compound of formula (X)), and b) coupling the compound of formula (X) with a compound selected from the group consisting of a compound of formula (XI), (XII) or (XIII) using a palladium (0) catalyst to prepare a protected derivative of a compound of formula (VII) wherein $Y^1$ is —C=C—, —C≡C—, —S— or —NR$^7$— (i.e., a compound of formula (VII-B)).

The conversion of a compound of formula (VIII-A) to the triflate compound of formula (X) may be carried out using a suitable triflating reagent. This reaction is typically carried out in an inert solvent using a base and a reagent designed for conversion of alcohols into triflates (i.e., a triflating reagent). Examples of suitable bases include but are not limited to sodium carbonate, trialkylamines, pyridine, sodium hydride, and lithium bis(trimethylsilyl) amide. The reaction is preferably run at a temperature of from about 0 to about 25° C. Suitable triflating reagents for this reaction include but are not limited to, trifluoromethanesulfonic anhydride, trifluoromethanesulfonyl chloride, and N-phenyltrifluoromethanesulfonimide. Suitable inert solvents for this reaction include but are not limited to tetrahydrofuran, dichloromethane, toluene, chloroform, diethyl ether, and dioxane.

The compound of formula (X) may then be reacted with a compound of formula (XI), (XII), or (XIII) using a palladium (0) catalyst. This reaction may be carried out in an inert solvent, in the presence of palladium (0). The reaction may optionally be heated to a temperature of from about 50 to about 150° C. Typically, the reaction is carried out by reacting an equimolar amount of a compound of formula (X) with an equimolar amount of the compound selected from the group consisting of compounds of formula (XI), (XII) and (XIII). The palladium (0) catalyst is typically present in 1-10 mole percent compared to the compound of formula (X). Examples of suitable palladium catalysts include but are not limited to, tetrakis(triphenylphosphine)-palladium (0) and tris(dibenzylideneacetone)dipalladium (0). It is also possible to generate the palladium (0) catalyst in situ using palladium (II) sources. Examples of suitable palladium (II) sources include but are not limited to, palladium (II) acetate, palladium (II) chloride, palladium (II) trifluoroacetate, dichlorobis(triphenyl-phosphino)palladium (II), and bis(diphenylphosphino-ferrocene)palladium (II) dichloride. Suitable solvents for this reaction include but are not limited to N,N-dimethylformamide, tetrahydrofuran, dioxane, toluene, benzene, 1,2-dimethoxyethane, and 1-methyl-2-pyrrolidinone. Bases and phosphines may be included as additives in the reaction if desired.

Examples of suitable bases include but are not limited to cesium carbonate, sodium carbonate, and trialkylamines. Examples of suitable phosphine additives include but are not limited to triphenylphosphine, tributylphosphine, diphenylphosphinoethane, and 2,2'-bis(diphenylphosphino)-1,1'-binaphthyl. Compounds of the formula (XI), (XII) and (XIII) may be obtained from commercial sources or prepared either as discreet compounds or generated in situ using conventional knowledge in the art. See, Luker, T. J., et al., *Tetrahedron Lett.* 41:7731-7735 (2000); Yin, J., et al., *Org. Lett.* 2:1101-1104 (2000); Wolfe, J. P., et al., *Can. J. Chem.* 78:957-962 (2000); Littke, A. F., et al., *J. Am. Chem. Soc.* 122:4020-4028 (2000); Hundertmark, T., et al., *Org. Lett.* 2:1729-1731 (2000); Buchwald, S. L., *Acc. Chem. Res.* 31:805-818 (1998); Suzuki, A., *J. Organomet. Chem.* 576:147-168 (1999); Negishi, E., *J. Organomet. Chem.* 576:179-194 (1999); Stanforth, S. P., *Tetrahedron* 54:263-303 (1998); Littke, A. F., *Angew. Chem., Int. Ed.* 37:3387-3388 (1999); and Thorand, S., et al., *J. Org. Chem.* 63:8551-8553 (1998). The reaction yields a protected derivative of the compound of formula (VII) wherein $Y^1$ is —C=C—, —C≡C—, —S— or —NR$^7$— (i.e., a compound of formula (VII-B)).

The compound of formula (VII) is obtained from a compound of formula (VII-A) or (VII-B) by removal of the protecting group. Methods for the removal of nitrogen protecting groups are conventional in the art any suitable method for the removal of the protecting group may be employed.

The compound of formula (VIII) can be prepared by reacting a compound of formula (XIV) with thiourea.

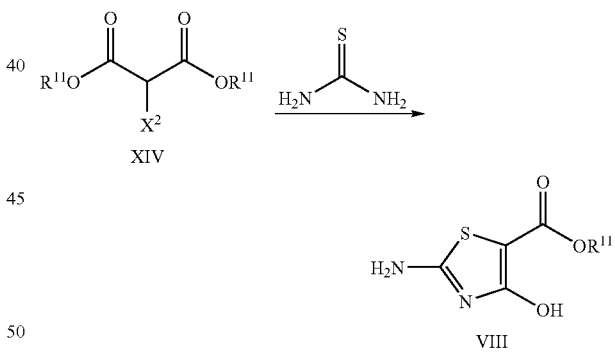

wherein:

$R^{11}$ is alkyl;

$X^2$ is Cl or Br; and all other variables are as defined above.

This reaction is carried out according to the procedures described in Baldwin, J. J., et. al. *J. Med. Chem.* 1980, 23, 65-70.

The compounds of formula (XIV) are commercially available or may be prepared using conventional reagents and techniques.

A compound of formula (III) can be prepared by several methods. According to one method, a compound of formula (III) is prepared according to Scheme 3 below.

Scheme 3

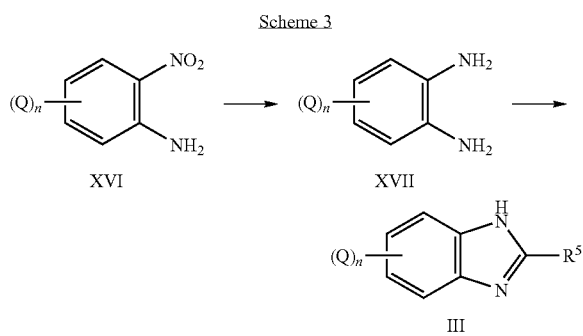

wherein all variables are as defined in connection with Scheme 1.

Generally, this process for preparing a compound of formula (III) comprises the steps of:
a) reducing the compound of formula (XVI) to prepare a compound of formula (XVII); and
b) reacting the compound of formula (XVII) with a ring forming reagent to prepare a compound of formula (III).

The order of the foregoing steps is not critical to the practice of the invention and the process may be practiced by performing the steps in any suitable order based on the knowledge of those skilled in the art.

More specifically, a compound of formula (III) can be prepared by reacting a compound of formula (XVII) with a ring forming reagent. There are several ring forming reagents which may be employed in this process step. In one embodiment, the compound formula (III-A) (i.e., a compound of formula (III) wherein $R^5$ is H or alkyl) is prepared by reacting a compound of formula (XVII) with a ring forming reagent of formula (XVIII).

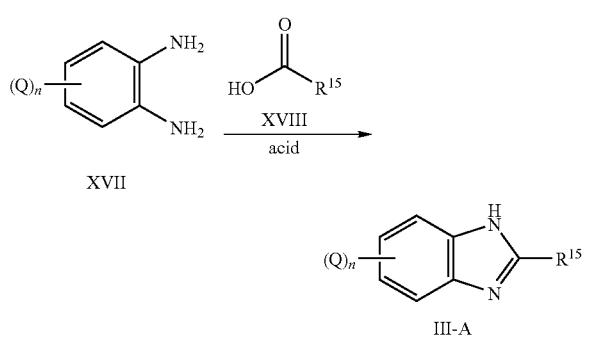

wherein $R^{15}$ is H or alkyl and all other variables are as defined above.

This reaction may be carried out using conventional techniques. See, White, A., et al., *J. Med. Chem.* 43:4084-4097 (2000); Jiang, J.-L., et al., *Synthetic Comm.* 28:4137-4142 (1998); Tanaka, A., et al., *Chem. Pharm. Bull.* 42:560-569 (1994); Tian, W., et al., *Synthesis* 12:1283-1286 (1992); Buckle, D. R., et al., *J. Med. Chem.* 30:2216-2221 (1987); and Raban, M., et al., *J. Org. Chem.* 50:2205-2210 (1985). This reaction may be carried out neat or in a suitable solvent. The reaction may optionally be heated to a temperature of from about 50 to about 230° C. The reaction is typically carried out with an excess of the compound of formula (XVIII). An additional acid may be used. Examples of suitable acids include but are not limited to, hydrochloric acid, hydrobromic acid, perchloric acid, sulfuric acid, p-toluenesulfonic acid, methanesulfonic acid, and trifluoromethanesulfonic acid. Examples of suitable solvents for this reaction include but are not limited to water, methanol, ethanol, isopropanol, tetrahydrofuran, dichloromethane, toluene, N,N-dimethylformamide, dimethylsulfoxide, and acetonitrile. The compounds of formula (XVIII) are commercially available.

A compound of formula (XVII) may be prepared by reducing a compound of formula (XVI). The reduction can be carried out using conventional techniques and reducing agents. See, Rangarajan, M., et al., *Bioorg. Med. Chem.* 8:2591-2600 (2000); White, A. W., et al., *J. Med. Chem.* 43: 4084-4097 (2000); Silvestri, R., et al., *Bioorg. Med. Chem.* 8:2305-2309 (2000); Nagaraja, D., et al., *Tetrahedron Lett.* 40:7855-7856 (1999); Jung, F., et al., *J. Med. Chem.* 34:1110-1116 (1991); Srivastava, R. P., et al., *Pharmazie* 45:34-37 (1990); Hankovszky, H. O., et al., *Can. J. Chem.* 67:1392-1400 (1989); Ladd, D. L., et al., *J. Org. Chem.* 53:417-420 (1988); Mertens, A., et al., *J. Med. Chem.* 30:1279-1287 (1987); and Sharma, K. S., et al., *Synthesis* 4:316-318 (1981). Examples of suitable reducing agents for this reaction include but are not limited to, palladium with hydrogen, palladium with ammonium formate, platinum oxide with hydrogen, nickel with hydrogen, tin(II) chloride, iron with acetic acid, aluminum with ammonium chloride, borane, sodium dithionite, and hydrazine. The reaction may optionally be heated to between about 50 and about 120° C. Suitable solvents for this reaction vary and include but are not limited to, water, methanol, ethanol, ethyl acetate, tetrahydrofuran, and dioxane.

A compound of formula (XVI) may be prepared by several methods. In one embodiment, the compound of formula (XVI) is prepared by reacting a compound of formula (XIX) with ammonia.

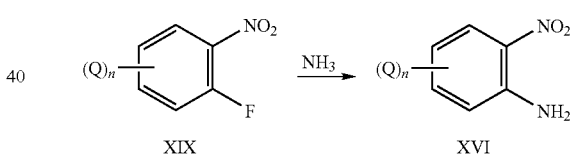

wherein all variables are as defined above.

This reaction may be carried out using conventional techniques. See, Silvestri, R., et al., *Bioorg. Med. Chem.* 8:2305-2309 (2000); Hankovszky, H. O., et al., *Can. J. Chem.* 67:1392-1400 (1989); Nasielski-Hinkens, R.; et al., *Heterocycles* 26:2433-2442 (1987); Chu, K. Y., et al., *J. Chem. Soc., Perkin Trans.* 1 10:1194-1198 (1978). This reaction is typically carried out with an excess of ammonia and may be optionally heated to a temperature of from about 50 to about 100° C. Examples of suitable solvents for this reaction include but are not limited to, water, methanol, ethanol, isopropanol, tetrahydrofuran, dioxane, and 1,2-dimethoxyethane.

The compounds of formula (XIX) are commercially available or may be prepared using conventional techniques and reagents.

In another embodiment, the compound of formula (XVI) can be prepared by reacting a protected compound of formula (XX) under nitration conditions to prepare a protected compound of formula (XVI) (i.e., XVI-A) and then removing the protecting group from the compound of formula (XVI-A).

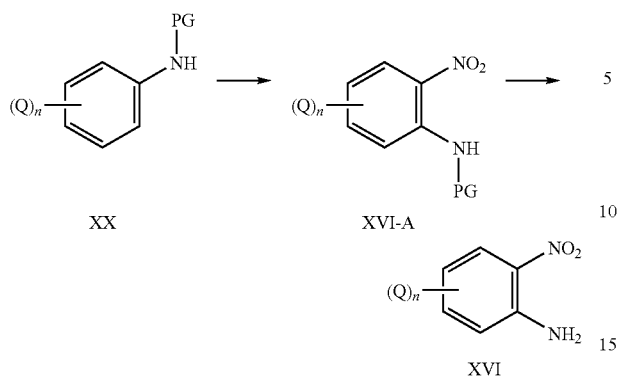

wherein PG is a protecting group and all other variables are as defined above.

The protection of anilines is a common transformation well known to one skilled in the art. See, Kocienski, P. J. *Protecting Groups*, Georg Thieme Verlag, Stuttgart, 1994; and Greene, T. W., Wuts, P. G. M. *Protecting Groups in Organic Synthesis* (2$^{nd}$ Edition), J. Wiley and Sons, 1991. Suitable protecting groups for this application include but are not limited to acetyl, trifluoroacetyl, benzyloxycarbonyl, allyloxycarbonyl, 2-(trimethylsilyl)ethoxycarbonyl, phenylsulfonyl, and p-toluenesulfonyl. Reagents and conditions vary according to the nature of the particular protecting group. Some typical reagents include but are not limited to acetic anhydride, trifluoroacetic anhydride, benzyl chloroformate, allyl chloroformate, 4-nitrophenyl 2-(trimethylsilyl)ethyl carbonate, phenylsulfonyl chloride, and p-toluensulfonyl chloride. In certain cases the addition of some base is required. Examples of suitable bases include but are not limited to potassium carbonate, sodium carbonate, trialkylamines, pyridine, and potassium t-butoxide. Suitable solvents for these conversions include but are not limited to dichloromethane, chloroform, tetrahydrofuran, acetic acid, methanol, ethanol, water, toluene, and diethyl ether.

The nitration of anilines is also well documented in the literature and the foregoing reaction may be carried out using these conventional techniques. See, Wissner, A., et. al., *J. Med. Chem.* 46: 49-63 (2003); Duggan, S. A., et. al., *J. Org. Chem.* 66: 4419-4426 (2001); Clews, J., et. al., *Tetrahedron* 56: 8735-8746 (2000); and Kagechika, H., *J. Med. Chem.* 31: 2182-2192 (1988). The nitration may be carried out with a variety of nitrating reagents including but not limited to 70% aqueous nitric acid, red fuming nitric acid, ammonium nitrate with trifluoroacetic anhydride, and potassium nitrate with trifluoromethanesulfonic acid. The reaction is typically conducted at room temperature, but may be optionally heated to a temperature of from about 40 to about 100° C. in certain cases. Suitable solvents include but are not limited to acetic acid, sulfuric acid, acetic anhydride, dichloromethane, and chloroform.

The nitration results in a compound of formula (XVI-A), (i.e., a protected derivative of the compound of formula (XVI)). The cleavage of the aniline protecting group, to result in a compound of formula (XVI) can be accomplished through many different conventional methods. See, Kocienski, P. J. *Protecting Groups*, Georg Thieme Verlag, Stuttgart, 1994; and Greene, T. W., Wuts, P. G. M. *Protecting Groups in Organic Synthesis* (2$^{nd}$ Edition), J. Wiley and Sons, 1991.

The compounds of formula (XX) may be prepared by installing a protecting group on the corresponding aniline. Such anilines are commercially available or may be prepared using conventional techniques.

A compound of formula (III-B) may optionally be converted to a compound of formula (III-C). This conversion may be effected by halogenating the compound of formula (III-B) to prepare a compound of formula (III-C).

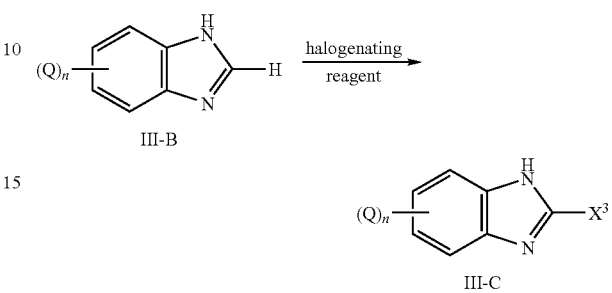

wherein $X^3$ is halo (particularly Cl, Br or I) and all other variables are as defined above.

This type of transformation is well established in the literature. See, Taylor, E. C., et al., *J. Org. Chem.* 56:6937-6939 (1991); Mistry, A. G., et al., *Tetrahedron Lett* 27:1051-1054 (1986); and Apen, P. G., et al., *Heterocycles* 29:1325-1329 (1989). Suitable halogenating agents include but are not limited to, N-chlorosuccinimide, N-bromosuccinimide, N-iodosuccinimide, chlorine, bromine, and iodine. Examples of suitable solvents include but are not limited to, dichloromethane, chloroform, diethyl ether, tetrahydrofuran, and acetone.

A compound of formula (III-C) may also be prepared directly from a compound of formula (XVII). The process comprises the steps of i) reacting a compound of formula (XVII) with a phosgene or phosgene equivalent compound to prepare a compound of formula (XXI) and ii) reacting the compound of formula (XXI) with phosphorous oxy halide to prepare a compound of formula (III-C).

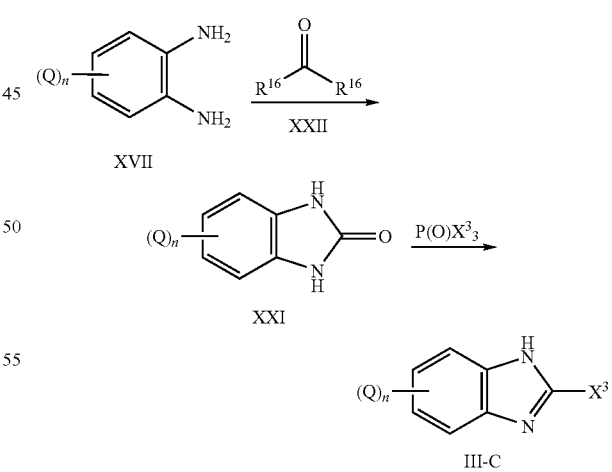

wherein:
each $R^{16}$ is the same or different and is independently selected from the group consisting of Cl, methoxy, ethoxy, trichloromethoxy, amino and N-imidazolyl;
$X^3$ is halo (particularly Cl, Br or I; more particularly Cl or Br); and
all other variables are as defined above.

The phosgene or phosgene equivalent compound is the ring forming reagent and is typically a compound of formula (XXII) as shown above. Phosgene and phosgene equivalent compounds of formula (XXII) are commercially available. Examples of suitable compounds of formula (XXII) include but are not limited to phosgene, dimethyl carbonate, diethyl carbonate, 1,1'-carbonyldiimidazole, urea, and triphosgene. The reaction of a compound of formula (XVII) with the phosgene or phosgene equivalent compound can be carried out using conventional techniques. See, Silvestri, R., et al., Bioorg. Med. Chem. 8:2305-2309 (2000); Wright, J. L., et al., J. Med. Chem. 43:3408-3419 (2000); Penieres, G. C., et al., Synthetic Comm. 30:2191-2195 (2000); and Von der Saal, W., et al., J. Med. Chem. 32:1481-1491 (1989). The reaction is typically run in an inert solvent or neat. The reaction may be optionally heated to a temperature of from about 50 to about 250° C. The optional addition of a suitable base to the reaction may be desirable. Examples of such bases include but are not limited to, trialkylamines, pyridine, 2,6-lutidine, potassium carbonate, sodium carbonate, and sodium bicarbonate. Examples of suitable solvents for this reaction include but are not limited to dichloromethane, chloroform, N,N-dimethylformamide, tetrahydrofuran, toluene, and acetone.

The reaction of the compound of formula (XXI) with the phosphorous oxy halide to prepare a compound of formula (III-C) can be carried out using conventional techniques. See, Blythin, D. J., et al., J. Med. Chem. 29:1099-1113 (1986); and Crank, G., Aust. J. Chem. 35:775-784 (1982). Examples of suitable reagents include but are not limited to phosphorous oxychloride and phosphorous oxybromide. Suitable solvents include but are not limited to, dichloromethane, chloroform, dichloroethane, and toluene. Optional heat ranging from about 50 to about 150° C. may be used.

A compound of formula (III-C), prepared by any method, may optionally be converted to a compound of formula (III-D) by reacting with an amine of formula $HNR^7R^8$.

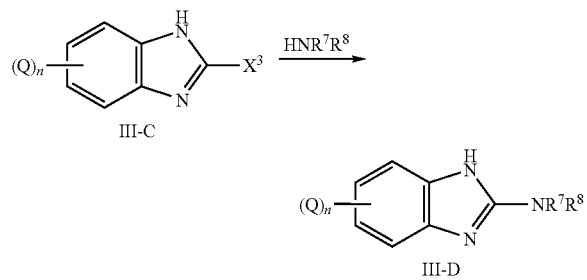

wherein all variables are as defined above.

The reaction of a halo-substituted benzimidazole of formula (III-C) with an amine to prepare a compound of formula (III-D) can be carried out using conventional techniques. See, Alcalde, E., et al., J. Org. Chem. 56:4233-4238 (1991); Katsushima, T., et al., J. Med. Chem. 33:1906-1910 (1990); Young, R. C., et al., J. Med. Chem. 33:2073-2080 (1990); Iemura, R., et al., J. Med. Chem. 29:1178-1183 (1986); and Benassi, R., et al., J. Chem. Soc., Perkin Trans. 210:1513-1521 (1985). An acid catalyst may be employed if desired. Examples of suitable acid catalysts include but are not limited to, hydrochloric acid and p-toluenesulfonic acid. The reaction can optionally be heated to a temperature of from about 50 to about 220° C. Suitable solvents for this reaction include but are not limited to, water, ethanol, isopropanol, 1-methyl-2-pyrrolidinone, N,N-dimethylformamide, dimethylsulfoxide, toluene, xylenes and tetrahydrofuran.

In another embodiment, a compound of formula (III-E) (i.e., a compound of formula (III) wherein $R^5$ is H or alkyl) is prepared according to the process outlined in Scheme 4 below.

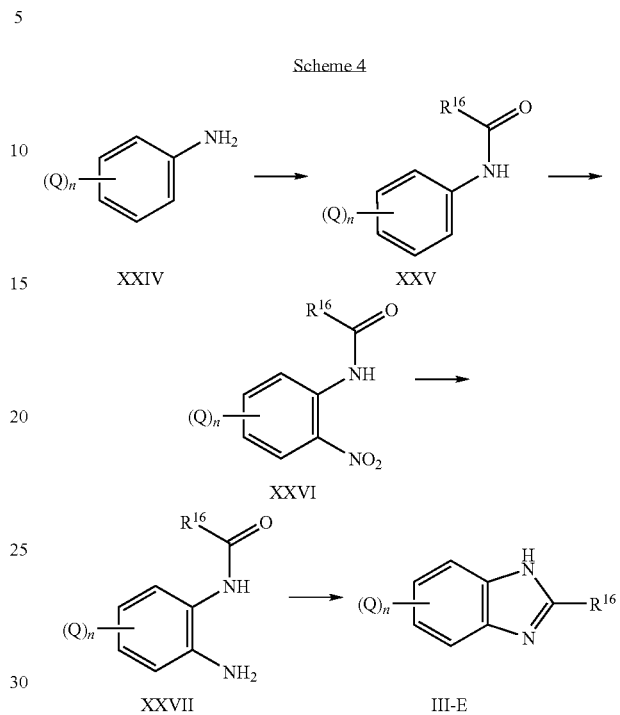

Scheme 4 wherein $R^{16}$ is H or alkyl and all other variables are as defined above.

Generally, this process for preparing a compound of formula (III-E) comprises the steps of:
a) reacting a compound of formula (XXIV) with a suitable acylating agent to prepare a compound of the formula (XXV);
b) reacting a compound of formula (XXV) under nitration conditions to prepare a compound of the formula (XXVI);
c) reducing a compound of formula (XXVI) to prepare a compound of formula (XXVII); and
d) cyclizing a compound of formula (XXVII) to prepare a compound of formula (III-E).

The order of the foregoing steps is not critical to the practice of the invention and the process may be practiced by performing the steps in any suitable order based on the knowledge of those skilled in the art.

Conventional cyclization reactions for which may be used for the cyclization of the compound of formula (XXVII) to prepare a compound of formula (III-E) are well documented in the literature. See, Brañia, M. F., et. al., J. Med. Chem. 45: 5813-5816 (2002); Fonseca, T., et. al., Tetrahedron 57: 1793-1799 (2001); White, A. W., et. al., J. Med. Chem. 43: 4084-4097 (2000); and Tamura, S. Y., et. al., Biorg. Med. Chem. Lett. 7:1359-1364 (1997). The reaction may be carried out neat or in a suitable solvent. The reaction may optionally be heated to a temperature of from about 50 to about 200° C. Typically an excess of a suitable acid is used. Examples of suitable acids include but are not limited to acetic acid, trifluoroacetic acid, hydrochloric acid, hydrobromic acid, sulfuric acid, methanesulfonic acid, p-toluenesulfonic acid, and pyridinium p-toluenesulfonate. A dehydrating reagent may optionally be used as well. Examples of suitable dehydrating reagents include but are not limited to magnesium sulfate, sodium sulfate, phosphorous pentoxide, and molecular sieves. Examples of suitable solvents include but are not limited to dichloromethane, chloroform, toluene, xylenes, methanol, ethanol, and water.

A compound of formula (XXVII) may be prepared by reducing a compound of formula (XXVI). The reduction can be carried out using conventional techniques and reducing agents. See, Rangarajan, M., et al., *Bioorg. Med. Chem.* 8:2591-2600 (2000); White, A. W., et al., *J. Med. Chem.* 43: 4084-4097 (2000); Silvestri, R., et al., *Bioorg. Med. Chem.* 8:2305-2309 (2000); Nagaraja, D., et al., *Tetrahedron Lett.* 40:7855-7856 (1999); Jung, F., et al., *J. Med. Chem.* 34:1110-1116 (1991); Srivastava, R. P., et al., *Pharmazie* 45:34-37 (1990); Hankovszky, H. O., et al., *Can. J. Chem.* 67:1392-1400 (1989); Ladd, D. L., et al., *J. Org. Chem.* 53:417-420 (1988); Mertens, A., et al., *J. Med. Chem.* 30:1279-1287 (1987); and Sharma, K. S., et al., *Synthesis* 4:316-318 (1981). Examples of suitable reducing agents for this reaction include but are not limited to, palladium with hydrogen, palladium with ammonium formate, platinum oxide with hydrogen, nickel with hydrogen, tin(II) chloride, iron with acetic acid, aluminum with ammonium chloride, borane, sodium dithionite, and hydrazine. The reaction may optionally be heated to between about 50 and about 120° C. Suitable solvents for this reaction vary and include but are not limited to, water, methanol, ethanol, ethyl acetate, tetrahydrofuran, and dioxane.

A compound of formula (XXVI) may be prepared by reacting a compound of formula (XXV) under nitration conditions. The reaction of the compound of formula (XXV) under nitration conditions may be carried out in the same manner as described above for the nitration of a compound of formula (XX).

A compound of formula (XXV) may be prepared by acylating a compound of formula (XXIV). Acylation of anilines is a common transformation well known to one skilled in the art and such conventional acylation techniques may be employed for carrying out the foregoing reaction. See, Larock, R. C. *Comprehensive Organic Transformations*, VCH Publishers, Inc., New York, pp. 972-976, 979, 981 (1989). The acylation reaction is typically carried out using an acylating agent such as an acid halide, acid anhydride, or carboxylic acid, in the presence of a coupling reagent(s). Examples of suitable coupling reagents include but are not limited to N,N-dicyclohexylcarbodiimide, 1-(3-dimethylaminopropyl)-3-ethylcarbodiimide hydrochloride, O-(7-azabenzotriazol-1-yl)-N,N,N',N'-tetramethyluronium hexafluorophosphate, and N,N'-carbonyldiimidazole. Suitable solvents include but are not limited to N,N-dimethylformamide, tetrahydrofuran, dioxane, toluene, benzene, 1,2-dimethoxyethane, and 1-methyl-2-pyrrolidinone. Anilines of formula (XXIV) are commercially available or readily prepared from commercially available material using conventional techniques.

As will be apparent to those skilled in the art, a compound of formula (I) may be converted to another compound of formula (I) using techniques well known in the art. For example, a compound of formula (I-A) may be converted to a compound of formula (I-B), which may in turn be converted to a compound of formula (I-C), or a compound of formula (I-A) may be converted to a compound of formula (I-C).

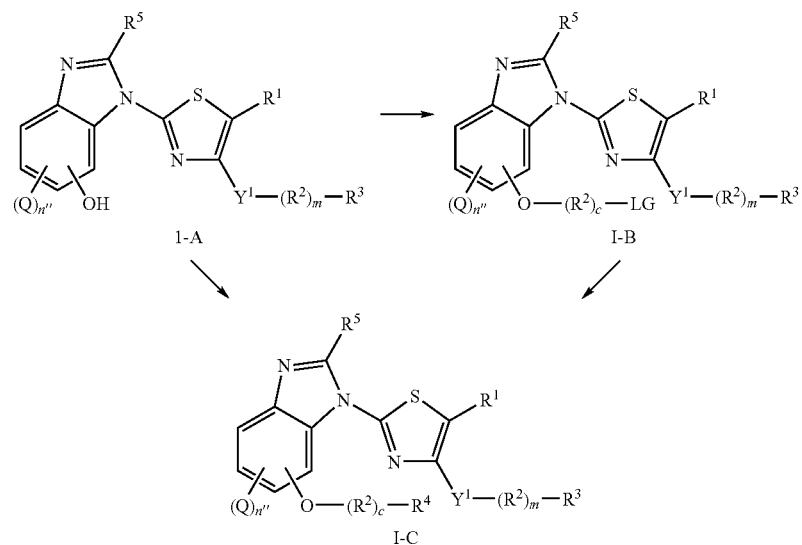

wherein
n" is 0, 1, 2 or 3;
each LG is the same or different suitable leaving group; and
all other variables are as defined above.

Compounds of formula (I-A) may be prepared according to any of the methods described herein above. The compound of formula (I-A) may then be converted to a compound of formula (I-B) or a compound of formula (I-C).

The compound of formula (I-B) may be prepared by either of two methods. According to one method, a compound of formula (I-B) is prepared by reacting a compound of formula (I-A) with a compound of formula: LG-$(R^2)_c$-LG (XXX), wherein all variables are as defined above. Specific examples of suitable leaving groups include but are not limited to —Cl, —Br, —I, —OSO$_2$CH$_3$ and —OSO$_2$-Phenyl. Suitable compounds of formula (XXX) are commercially available or may be prepared using conventional techniques. The reaction may be carried out in an inert solvent, conveniently at room temperature, in the presence of a suitable base. Examples of suitable bases for this reaction include but are not limited to, potassium carbonate, sodium carbonate, cesium carbonate, sodium hydride, and potassium hydride. Examples of suitable inert solvents for this reaction include but are not limited to, N,N-dimethylformamide, tetrahydrofuran, dioxane, and 1,2-dimethoxyethane.

According to a second method, a compound of formula (I-B) is prepared by reacting a compound of formula (I-A) with a compound of formula: HO—(R$^2$)$_c$-LG (XXXI), wherein all variables are as defined above. Specific examples of suitable leaving groups include those described above. Compounds of formula (XXXI) are commercially available or can be prepared using conventional techniques. The reaction is carried out in an inert solvent under standard Mitsunobu conditions. See, Hughes, D. L., Org. React. 42:335-656 (1992); and Mitsunobu, O., Synthesis 1-28 (1981). Typically the compound of formula (I-A) and the compound of formula (XXXI) are reacted together with a triarylphosphine, and a dialkyl azodicarboxylate at room temperature. Examples of suitable triarylphosphines include but are not limited to, triphenylphosphine, tri-tolylphosphine, and tri-mesitylphosphine. Examples of suitable dialkyl azodicarboxylates include but are not limited to, diethyl azodicarboxylate, diisopropyl azodicarboxylate, and di-tert-butyl azodicarboxylate. Examples of suitable inert solvents for this reaction include but are not limited to, tetrahydrofuran, dioxane, 1,2-dimethoxyethane, dichloromethane, and toluene.

The compound of formula (I-B) may be converted to a compound of formula (I-C) by reaction with a suitable nucleophile for installing the group R$^4$. Examples of suitable nucleophiles include but are not limited to ammonia, primary and secondary amines, metal alkoxides, metal thioalkoxides, potassium cyanide, sodium azide, organolithium reagents, organocuprates, and Grignard reagents. The specific conditions for these displacements vary, but the use of these types of nucleophiles for the installation of a group as defined by R$^4$ are conventional in the art. Displacement of the leaving group with such a nucleophile would either install the R$^4$ functionality or provide an intermediate from which the R$^4$ functional group could be readily installed according to conventional methods by one skilled in the art.

Alternatively, a compound of formula (I-C) may be prepared directly from a compound of formula (I-A) using procedures analogous to those described above for the conversion of a compound of formula (I-A) to a compound of formula (I-B). More specifically, a compound of formula (I-C) may be prepared by reacting a compound of formula (I-A) with a compound of formula: LG-(R$^2$)$_c$—R$^4$ (XXXII) using conditions analogous to those described above for the reaction of a compound of formula (I-A) with a compound of formula (XXX). Compounds of formula (XXXII) are commercially available or can be prepared using conventional techniques.

In another embodiment, a compound of formula (I-A) is converted to a compound of formula (I-C) by reacting with a compound of formula: HO—(R$^2$)$_c$—R$^4$ (XXXIII) under the conditions described above for the reaction of a compound of formula (I-A) with a compound of formula (XXXI). Compounds of formula (XXXIII) are commercially available or can be prepared using conventional techniques.

As a further example, a compound of formula (I-D) may be converted to a compound of formula (I-E), which may optionally be further converted to a compound of formula (I-F).

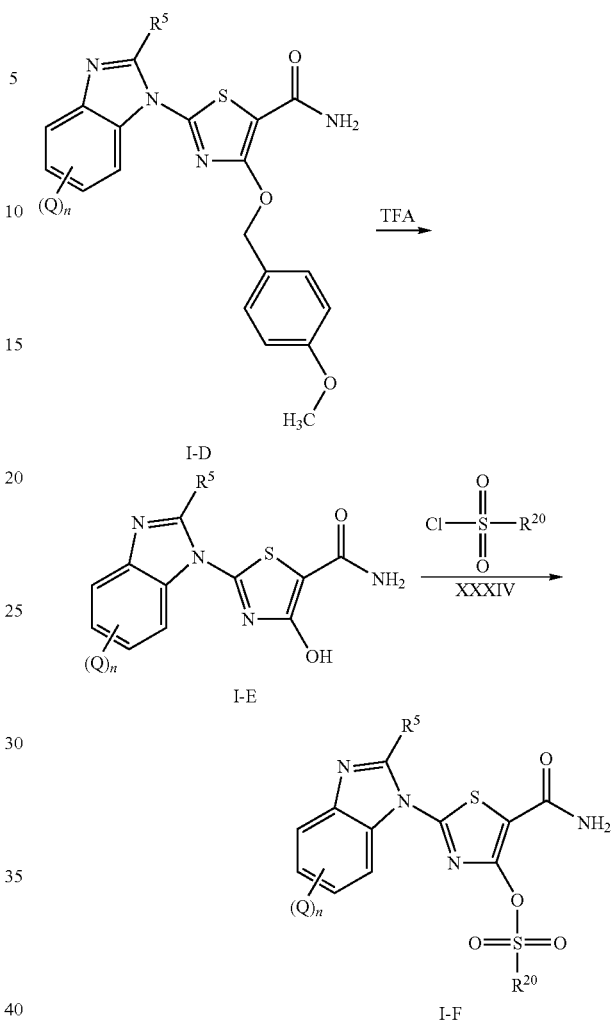

wherein:

R$^{20}$ is alkyl or phenyl; and all other variables are as defined above.

A compound of formula (I-D) may be converted to a compound of formula (I-E) by reacting with a suitable acid, such as trifluoroacetic acid (TFA). This reaction may be carried out neat or in an inert solvent at ambient temperature. Suitable solvents for this reaction include but are not limited to, dichloromethane and chloroform.

The compound of formula (I-E) may be further converted to a compound of formula (I-F) by reacting with sulfonyl chlorides of formula (XXXIV). The reaction may be carried out in an inert solvent at ambient temperature using a variety of bases. Examples of suitable bases include but are not limited to, triethylamine, N,N-diisopropylethylamine, and pyridine. Suitable solvents for this reaction include but are not limited to, dichloromethane, chloroform, tetrahydrofuran, 1,2-dimethoxyethane, dioxane, and N,N-dimethylformamide.

In another embodiment, a compound of formula (I-G) may be converted to a compound of formula (I-H). A compound of formula (I-H) may be further converted to a compound of formula (I-J).

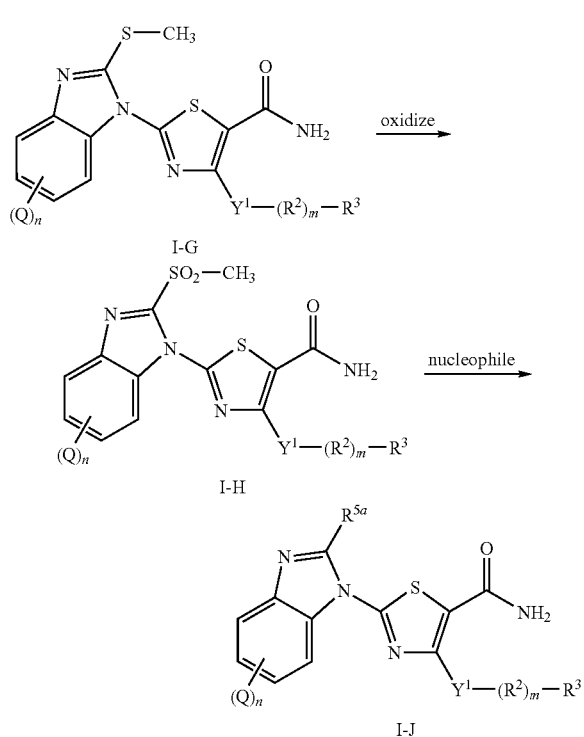

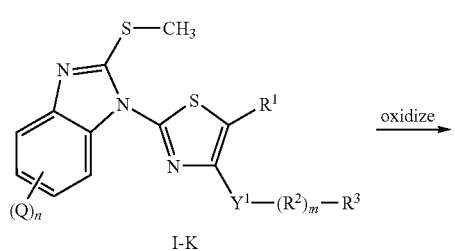

wherein $R^{5a}$ is selected from the group consisting of —$OR^7$ and —$NR^7R^8$;

and all other variables are as defined above.

A compound of formula (I-G) may be oxidized to a compound of formula (I-H) using a conventional oxidizing agent, such as for example, 3-chloroperoxybenzoic acid. Reaction of the compound of formula (I-H) with a suitable nucleophile of formula $R^{5a}$ will convert a compound of formula (I-H) to a compound of formula (I-J). Specific examples of suitable nucleophiles for this reaction include but are not limited to sodium hydroxide, sodium acetate, ammonia, and mono and di-substituted amines. The reaction with the nucleophile is typically carried out using equimolar or a slight excess of the nucleophile in an inert solvent, such as THF, at ambient or elevated temperatures. In another embodiment, a compound of formula (I-H) may be converted to a compound of formula (I-J) in a sealed tube at elevated temperatures between 80° C. and 120° C., using excess ammonia in an appropriate solvent such as methanol, ethanol, isopropanol, tetrahydrofuran and dioxane.

Similarly, a compound of formula (I-K) may also be converted to a compound of formula (I-L) by oxidation, and the compound of formula (I-L) may be converted to a compound of formula (I-M) by reaction with ammonia.

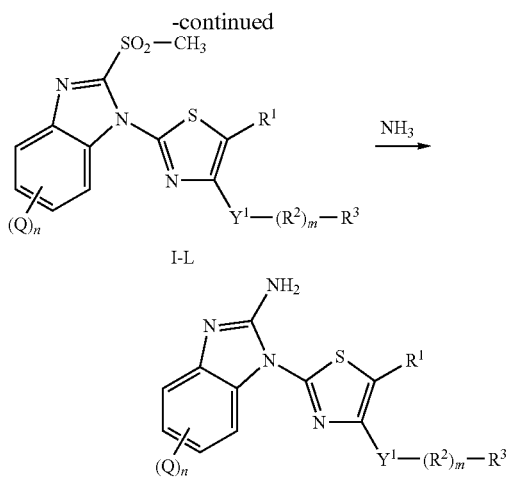

wherein all variables are as defined above.

The step of converting a compound of formula (I-K) to a compound of formula (I-L) may be carried out by reacting a compound of formula (I-K) with a suitable oxidizing agent, such as for example 3-chloroperoxybenzoic acid. The compound of formula (I-L) may be converted to a compound of formula (I-M) by reaction with excess ammonia in a sealed tube at elevated temperature between about 80 and about 120° C. in a suitable solvent. Suitable solvents for this reaction include but are not limited to methanol, ethanol, isopropanol, tetrahydrofuran and dioxane.

In yet another example of a conversion using a coupling protocol a compound of formula (I-O) is prepared from a compound of formula (I-N) as follows.

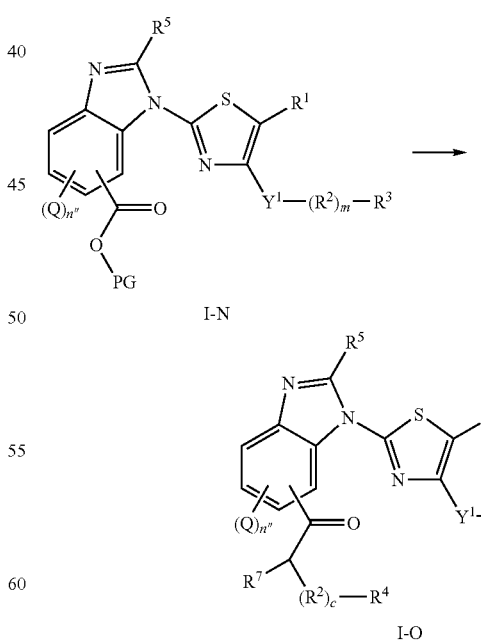

wherein n" is 0, 1, 2 or 3;
PG is a protecting group and
all other variables are as defined above.

The protecting group is typically carboxylic acid protecting group which when removed yields the acid. The cleavage of the carboxylic acid protecting group can be accomplished through many different methods conventional in the art. See, Kocienski, P. J. *Protecting Groups*, Georg Thieme Verlag, Stuttgart, 1994; and Greene, T. W., Wuts, P. G. M. *Protecting Groups in Organic Synthesis* (2$^{nd}$ Edition), J. Wiley and Sons, 1991.

Following the removal of the protecting group, the resulting carboxylic acid is reacted using a coupling protocol to yield the compound of formula (I-O). The reaction can be carried out by reacting the deprotected compound of formula (I-N) with a suitable coupling reagent in an inert solvent, followed by the addition of a primary or secondary amine, and optionally a base. Suitable coupling reagents include but are not limited to 1,1-carbonyldiimidazole, oxalyl chloride, dicyclohexylcarbodiimide and O-(7-azabenzotriazol-1-yl)-1,1,3,3-tetramethyluronium hexafluorophosphate. Suitable bases include but are not limited to triethylamine, diisoproylethylamine and the like. The reaction may be optionally heated to a temperature of from about 0° C. to about 80° C. Examples of suitable solvents include but are not limited to dimethylformamide, dichloromethane and tetrahydrofuran.

In yet another example of a conversion using a coupling protocol a compound of formula (I-Q) is prepared from a compound of formula (I-P) as follows.

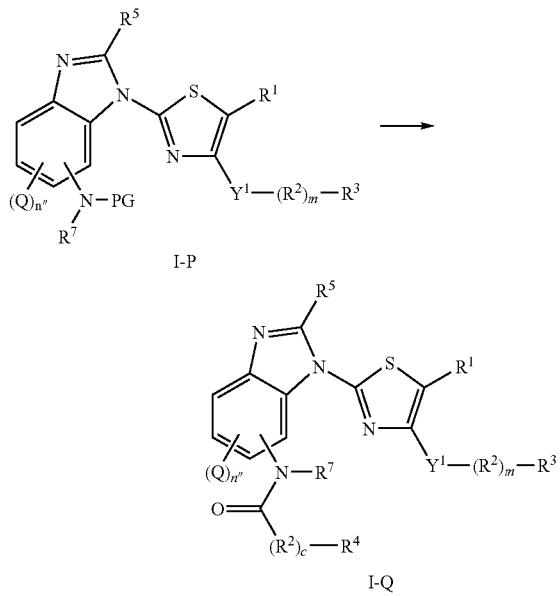

I-P

I-Q wherein n' is 0, 1, 2 or 3;
PG is a protecting group and
all other variables are as defined in any of Schemes 1-5 above.

The protecting group is amino protecting group which when removed yields the amine. The cleavage of the amino protecting group can be accomplished through many different methods conventional in the art. See, Kocienski, P. J. *Protecting Groups*, Georg Thieme Verlag, Stuttgart, 1994; and Greene, T. W., Wuts, P. G. M. *Protecting Groups in Organic Synthesis* (2$^{nd}$ Edition), J. Wiley and Sons, 1991.

Following the removal of the protecting group, the resulting amine is reacted using a coupling protocol to yield the compound of formula (I-Q). The reaction can be carried out by reacting the deprotected compound of formula (I-P) with a carboxylic acid in the presence of a suitable coupling reagent in an inert solvent, and optionally a base. Suitable coupling reagents include but are not limited to 1,1-carbonyldiimidazole, oxalyl chloride, dicyclohexylcarbodiimide and O-(7-azabenzotriazol-1-yl)-1,1,3,3-tetramethyluronium hexafluorophosphate. Suitable bases include but are not limited to triethylamine, diisoproylethylamine and the like. The reaction may be optionally heated to a temperature of from about 0° C. to about 80° C. Examples of suitable solvents include but are not limited to dimethylformamide, dichloromethane and tetrahydrofuran.

A further example of a process for converting a compound of formula (I) to a different compound of formula (I) includes the reaction of a compound of formula (I-R) with a thionating reagent to prepare a compound of formula (I-S).

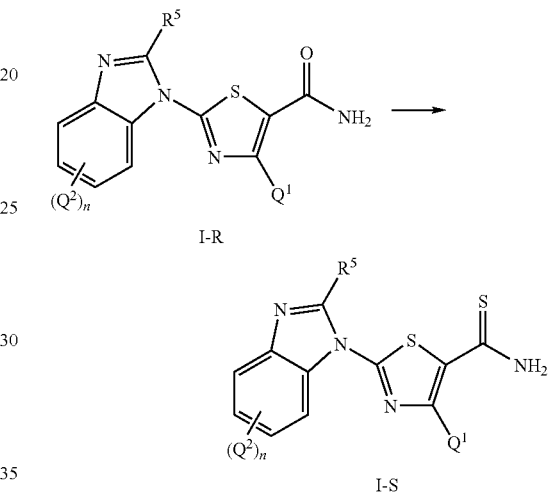

I-R

I-S wherein all variables are as defined in connection with Schemes 1-4 above.

The reaction may be carried out in an inert solvent and optionally heated to a temperature of from about 65 to above about 100° C. Examples of suitable thionating reagents include but are not limited to phosphorus pentasulfide, 2,4-bis(4-methoxyphenyl)-1,3-dithia-2,4-diphosphetane-2,4-disulfide and the like. Suitable solvents include but are not limited to xylene, dioxane and toluene.

Based upon this disclosure and the examples contained herein one skilled in the art can readily convert a compound of formula (I) or a pharmaceutically acceptable salt, solvate or physiologically functional derivative thereof into another compound of formula (I), or a pharmaceutically acceptable salt, solvate or physiologically functional derivative thereof.

The present invention also provides radiolabeled compounds of formula (I) and biotinylated compounds of formula (I) and solid-support-bound versions thereof. Radiolabeled compounds of formula (I) and biotinylated compounds of formula (I) can be prepared using conventional techniques. For example, radiolabeled compounds of formula (I) can be prepared by reacting the compound of formula (I) with tritium gas in the presence of an appropriate catalyst to produce radiolabeled compounds of formula (I).

In one embodiment, the compounds of formula (I) are tritiated.

The radiolabeled compounds of formula (I) and biotinylated compounds of formula (I) are useful in assays for the identification of compounds which inhibit PLK, for the identification of compounds for the treatment of a condition mediated by PLK, for the treatment of susceptible neoplasms, for the treatment of conditions characterized by inappropriate proliferation, for the inhibition of proliferation of a cell and for the inhibition of mitosis in a cell. Accordingly, the present invention provides an assay method for identifying such compounds, which method comprises the step of specifically binding the radiolabeled compound of formula (I) or the biotinylated compound of formula (I) to the target protein or cellular homogenates. More specifically, suitable assay methods will include competition binding assays. The radiolabeled compounds of formula (I) and biotinylated compounds of formula (I) and solid-support-bound versions thereof, can be employed in assays according to the methods conventional in the art.

The following examples are intended for illustration only and are not intended to limit the scope of the invention in any way, the invention being defined by the claims which follow.

Reagents are commercially available or are prepared according to procedures in the literature. In the following structures, "Me" refers to the group —CH$_3$.

INTERMEDIATE EXAMPLE 1

Ethyl 2-amino-4-hydroxy-1,3-thiazole-5-carboxylate

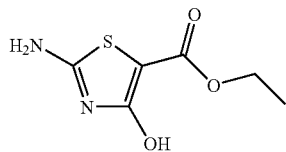

Prepared according to literature procedure (Baldwin, J. J., et al. *J. Med. Chem.* 1980, 23, 65-70.) from thiourea and diethyl bromomalonate. MS m/z 189 (m+1).

INTERMEDIATE EXAMPLE 2

Ethyl 2-(acetylamino)-4-hydroxy-1,3-thiazole-5-carboxylate

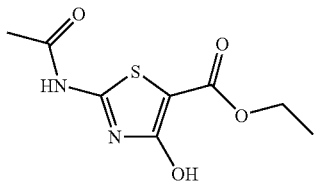

Ethyl 2-amino-4-hydroxy-1,3-thiazole-5-carboxylate (6.00 g, 31.9 mmol) was dissolved in 100 mL of acetic acid with stirring. Acetic anhydride (15.0 mL, 159 mmol) was added via syringe. The reaction was stirred for 16 hours and 100 mL of diethyl ether was added. The reaction was filtered and the pale yellow solid was washed with diethyl ether, dried, and collected to afford 6.04 g (82%) of ethyl 2-(acetylamino)-4-hydroxy-1,3-thiazole-5-carboxylate. $^1$H NMR (300 MHz, DMSO-d$_6$) δ 12.32 (s, 1H), 11.32 (s, 1H), 4.16 (q, J=7.0 Hz, 2H), 2.16 (s, 3H), 1.23 (t, J=7.0 Hz, 3H).

INTERMEDIATE EXAMPLE 3

Ethyl 2-(acetylamino)-4-({[2-(trifluoromethyl)phenyl]-methyl}oxy)-1,3-thiazole-5-carboxylate

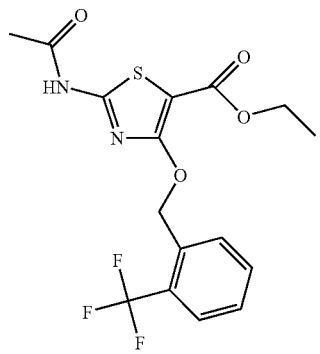

Ethyl 2-(acetylamino)-4-hydroxy-1,3-thiazole-5-carboxylate (6.04 g, 26.2 mmol) was dissolved in 100 mL of N,N-dimethylformamide with stirring. Potassium carbonate (3.98 g, 28.8 mmol) was added in a single portion. 2-Trifluoromethylbenzyl bromide (6.58 g, 27.5 mmol) in 20 mL of N,N-dimethylformamide was added via syringe. The reaction was stirred for 16 hours and poured into water and ethyl acetate. The layers were separated, and the organic layer was washed with brine. The combined aqueous layers were extracted with ethyl acetate. The combined organic layers were dried over MgSO$_4$, filtered, and concentrated in vacuo. Purification by flash chromatography afforded 6.23 g (61%) of ethyl 2-(acetylamino)-4-({[2-(trifluoromethyl)-phenyl]methyl}oxy)-1,3-thiazole-5-carboxylate. $^1$H NMR (300 MHz, DMSO-d$_6$) δ 12.62 (s, 1H), 7.92 (m, 1H), 7.82-7.71 (m, 2H), 7.58 (m, 1H), 5.60 (s, 2H), 4.19 (q, J=7.2 Hz, 2H), 2.17 (s, 3H), 1.25 (t, J=7.2 Hz, 3H).

INTERMEDIATE EXAMPLE 4

Ethyl 2-amino-4-({[2-(trifluoromethyl)phenyl]-methyl}oxy)-1,3-thiazole-5-carboxylate

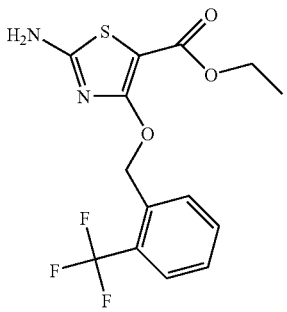

Ethyl 2-(acetylamino)-4-({[2-(trifluoromethyl)-phenyl]methyl}oxy)-1,3-thiazole-5-carboxylate (6.23 g, 16.0 mmol) was placed in a pressure vessel with a stir bar. 2N Ammonia in methanol (120 mL, 240 mmol) was added via syringe and the vessel was sealed. The solution was heated to 80° C. using an oil bath for 16 hours. The reaction was cooled and concentrated. The residue was dissolved in ethyl acetate and washed with half-saturated NaHCO$_3$ and brine. The combined aqueous layers were extracted with ethyl acetate. The combined organic layers were dried over MgSO$_4$, filtered, and concentrated in vacuo. The solid was dissolved in approximately 50 mL of dichloromethane, and 150 mL of hexanes was added. Air was blown over the solution and hexanes added periodically to precipitate the product. The solid was filtered, washed with hexanes, and air-dried to afford 4.80 g (87%) of ethyl 2-amino-4-({[2-(trifluoromethyl)-phenyl]methyl}oxy)-1,3-thiazole-5-carboxylate as a yellow solid. $^1$H NMR (400 MHz, DMSO-d$_6$) δ 8.14 (s, 2H), 7.90 (d, J=7.7 Hz, 1H), 7.81-7.72 (m, 2H), 7.57 (m, 1H), 5.52 (s, 2H), 4.11 (q, J=7.1 Hz, 2H), 1.21 (t, J=7.1 Hz, 3H).

INTERMEDIATE EXAMPLE 5

Ethyl 2-chloro-4-({[2-(trifluoromethyl)phenyl]-methyl}oxy)-1,3-thiazole-5-carboxylate

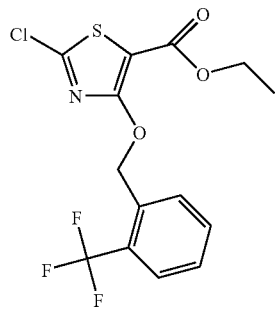

Copper(I) chloride (0.342 g, 3.45 mmol) and t-butyl nitrite (0.52 mL, 4.37 mmol) were stirred in 20 mL of acetonitrile. Ethyl 2-amino-4-({[2-(trifluoromethyl)-phenyl]methyl}oxy)-1,3-thiazole-5-carboxylate (1.00 g, 2.88 mmol) was added, and the reaction was stirred for 1.5 hours. The reaction was heated to 65° C. with an oil bath for an hour and cooled to room temperature. The reaction mixture was slowly pipeted onto 40 mL of 6N HCl stirring at 0° C. The ice bath was removed, and the mixture was warmed to room temperature, where it stirred for 30 minutes. The mixture was poured into ethyl acetate and water, and the layers were separated. The organic layer was washed with brine, and the combined aqueous layers were extracted with ethyl acetate. The combined organic layers were dried over MgSO$_4$, filtered, and concentrated in vacuo. The residue was purified by flash chromatography to provide 0.537 g (51%) of ethyl 2-chloro-4-({[2-(trifluoromethyl)phenyl]methyl}oxy)-1,3-thiazole-5-carboxylate. $^1$H NMR (400 MHz, DMSO-d$_6$) δ 7.88-7.73 (m, 3H), 7.60 (m, 1H), 5.63 (s, 2H), 4.24 (q, J=7.1 Hz, 2H), 1.25 (t, J=7.1 Hz, 3H).

INTERMEDIATE EXAMPLE 6

2-Chloro-4-({[2-(trifluoromethyl)phenyl]methyl}oxy)-1,3-thiazole-5-carboxylic acid

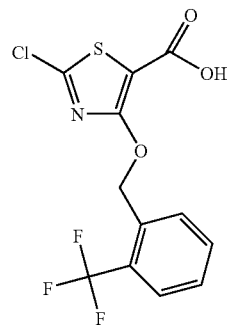

Ethyl 2-chloro-4-({[2-(trifluoromethyl)phenyl]methyl}oxy)-1,3-thiazole-5-carboxylate (0.535 g, 1.46 mmol) was dissolved in 15 mL of tetrahydrofuran with stirring, and 15 mL of 1N LiOH solution was added via pipet. The mixture was stirred for 18 hours, and poured into 0.1 N NaOH and diethyl ether. The layers were separated, and the aqueous layer was acidified to pH 2 with concentrated HCl. The mixture was filtered and the white solid was washed with water. The solid was air dried, collected, and dried further under vacuum to yield 0.418 g (85%) of 2-chloro-4-({[2-(trifluoromethyl)phenyl]methyl}oxy)-1,3-thiazole-5-carboxylic acid. $^1$H NMR (400 MHz, DMSO-d$_6$) δ 13.22 (br s, 1H), 7.83-7.70 (m, 3H), 7.58 (m, 1H), 5.59 (s, 2H).

INTERMEDIATE EXAMPLE 7

2-Chloro-4-({[2-(trifluoromethyl)phenyl]methyl}oxy)-1,3-thiazole-5-carboxamide

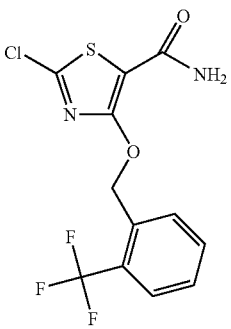

2-Chloro-4-({[2-(trifluoromethyl)phenyl]methyl}oxy)-1,3-thiazole-5-carboxylic acid (0.150 g, 0.444 mmol) was suspended in 5 mL of dichloromethane, and 1 drop of N,N-dimethylformamide was added with stirring. Oxalyl chloride (0.33 mL, 2.0M solution in dichloromethane, 0.66 mmol) was added dropwise via syringe. The reaction was stirred for 30 minutes and concentrated in vacuo. The residue was dissolved in 6 mL of tetrahydrofuran with stirring. 6 mL of 14% NH$_4$OH solution was added via pipet. The mixture was stirred for 30 minutes and poured into ethyl acetate and water, and the layers were separated. The organic layer was washed with brine, and the combined aqueous layers were extracted with ethyl acetate. The combined organic layers were dried over MgSO$_4$, filtered, and concentrated in vacuo to afford 0.147 g (98%) of 2-chloro-4-({[2-(trifluoromethyl)phenyl]methyl}oxy)-1,3-thiazole-5-carboxamide as a white solid. $^1$H NMR (400 MHz, DMSO-d$_6$) δ 7.86 (br s, 1H), 7.83-7.70 (m, 3H), 6.84 (br s, 1H), 5.62 (s, 2H).

EXAMPLE 1

2-(1H-Benzimidazol-1-yl)-4-({[2-(trifluoromethyl)phenyl]methyl}-oxy)-1,3-thiazole-5-carboxamide

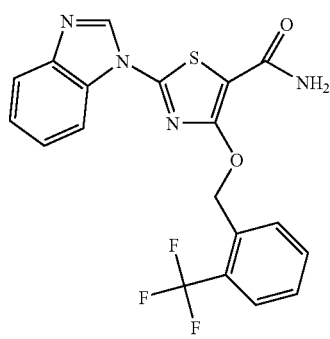

A solution of 2-chloro-4-({[2-(trifluoromethyl)phenyl]methyl}oxy)-1,3-thiazole-5-carboxamide (0.050 g, 0.14 mmol) and benzimidazole (0.010 g, 0.08 mmol) in DMF (4 mL) was heated at 75° C. in the presence of $K_2CO_3$ (0.011 g, 0.08 mmol) for 12 h. After the reaction mixture had cooled to rt, it was diluted with EtOAc (10 mL), washed with $H_2O$ (4×10 mL), dried over $MgSO_4$, filtered and concentrated in vacuo. The residue was purified by preparative HPLC to afford the title compound. $^1$H NMR (400 MHz, $CDCl_3$) δ 8.57 (s, 1H), 7.96 (d, J=7.7 Hz, 1H), 7.88 (d, J=7.7 Hz, 1H), 7.77 (d, J=7.7 Hz, 1H), 7.67-7.59 (m, 2H), 7.54-7.40 (m, 3H), 6.80 (bs, 1H), 5.82 (s, 2H), 5.63 (bs, 1H). MS m/z 419 (m+1).

EXAMPLE 2

2-(6-Chloro-1H-benzimidazol-1-yl)-4-({[2-(trifluoromethyl)phenyl]methyl}oxy)-1,3-thiazole-5-carboxamide and 2-(5-chloro-1H-benzimidazol-1-yl)-4-({[2-(trifluoromethyl)phenyl]methyl}oxy)-1,3-thiazole-5-carboxamide

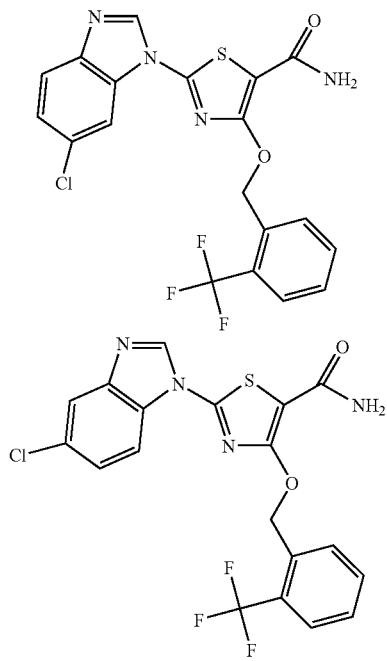

Following the procedure described above for the preparation of 2-(1H-benzimidazol-1-yl)-4-({[2-(trifluoromethyl)phenyl]methyl}oxy)-1,3-thiazole-5-carboxamide using the following materials: 2-chloro-4-({[2-(trifluoromethyl)phenyl]methyl}oxy)-1,3-thiazole-5-carboxamide (0.050 g, 0.14 mmol), 5-chlorobenzimidazole (0.012 g, 0.08 mmol), $K_2CO_3$ (0.011 g, 0.08 mmol) and DMF (4 mL). The regioisomeric mixture was separated by preparative HPLC. Data for (6-Cl): $^1$H NMR (400 MHz, $CDCl_3$) δ 8.47 (s, 1H), 7.98 (d, J=2.0 Hz, 1H), 7.81-7.75 (m, 2H), 7.68-7.60 (m, 2H), 7.55-7.50 (m, 1H), 7.39 (dd, J=8.6, 1.8 Hz, 1H), 6.81 (bs, 1H), 5.82 (s, 2H), 5.64 (bs, 1H). MS (ES–, m/z) 453 (m+1). Data for (5-Cl): $^1$H NMR (400 MHz, $CDCl_3$) δ 8.54 (s, 1H), 7.90-7.85 (m, 1H), 7.80-7.76 (m, 1H), 7.69-7.59 (m, 2H), 7.56-7.50 (m, 1H), 7.43 (dd, J=8.6, 2.0 Hz, 1H), 6.79 (bs, 1H), 5.81 (s, 2H), 5.55 (bs, 1H). MS m/z 453 (m+1).

EXAMPLE 3

2-(6-Methoxy-1H-benzimidazol-1-yl)-4-({[2-(trifluoromethyl)phenyl]methyl}oxy)-1,3-thiazole-5-carboxamide and 2-(5-methoxy-1H-benzimidazol-1-yl)-4-({[2-(trifluoromethyl)phenyl]methyl}oxy)-1,3-thiazole-5-carboxamide

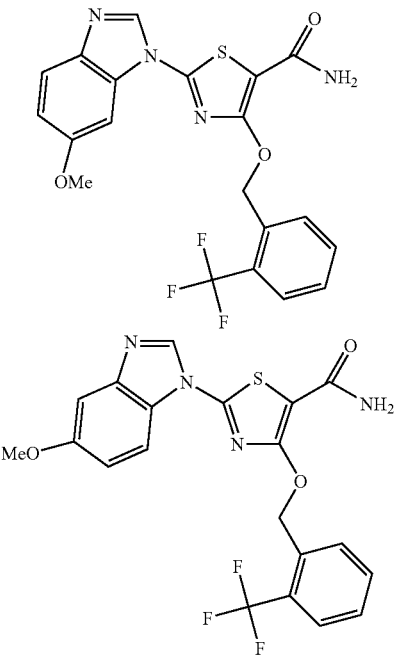

Following the procedure described above for the preparation of 2-(1H-benzimidazol-1-yl)-4-({[2-(trifluoromethyl)phenyl]methyl}oxy)-1,3-thiazole-5-carboxamide using the following materials: 2-chloro-4-({[2-(trifluoromethyl)phenyl]methyl}oxy)-1,3-thiazole-5-carboxamide (0.050 g, 0.14 mmol), 5-methoxybenzimidazole (0.012 g, 0.08 mmol), $K_2CO_3$ (0.011 g, 0.08 mmol) and DMF (4 mL). Data for mixture of 5 and 6 regioisomers: $^1$H NMR (400 MHz, $CDCl_3$) δ 8.49 (s, 0.5H), 8.44 (s, 0.5H), 7.84-7.71 (m, 2H), 7.69-7.58 (m, 2H), 7.54-7.49 (m, 1H), 7.46 (d, J=2.1 Hz, 1H), 7.34 (d, J=2.2 Hz, 1H), 7.04 (dd, J=8.9, 2.2 Hz, 0.5H), 7.02 (dd, J=8.8, 2.4 Hz, 0.5H), 6.78 (bs, 1H), 5.82 (s, 1H), 5.81 (s, 1H), 5.73 (bs, 1H), 3.89 (s, 1.5H), 3.88 (s, 1.5H). MS m/z 449 (m+1).

EXAMPLE 4

2-(6-Fluoro-1H-benzimidazol-1-yl)-4-({[2-(trifluoromethyl)phenyl]methyl}oxy)-1,3-thiazole-5-carboxamide

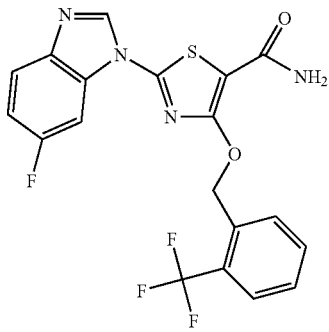

Following the procedure described above for the preparation of 2-(1H-benzimidazol-1-yl)-4-({[2-(trifluoromethyl)phenyl]methyl}oxy)-1,3-thiazole-5-carboxamide using the following materials: 2-chloro-4-({[2-(trifluoromethyl)phenyl]methyl}oxy)-1,3-thiazole-5-carboxamide (0.050 g, 0.14 mmol), 5-fluorobenzimidazole (0.011 g, 0.08 mmol), $K_2CO_3$ (0.011 g, 0.08 mmol) and DMF (4 mL). Data for 6 regioisomers: $^1$H NMR (400 MHz, $CDCl_3$) δ 8.46 (s, 1H), 7.82-7.74 (m, 2H), 7.69-7.58 (m, 3H), 7.54-7.50 (m, 1H), 7.16 (td, J=9.1, 2.4 Hz, 1H), 6.80 (bs, 1H), 5.82 (s, 2H), 5.76 (bs, 1H). MS m/z 437 (m+1).

EXAMPLE 5

2-(5,6-Dimethyl-1H-benzimidazol-1-yl)-4-({[2-(trifluoromethyl)phenyl]methyl}oxy)-1,3-thiazole-5-carboxamide

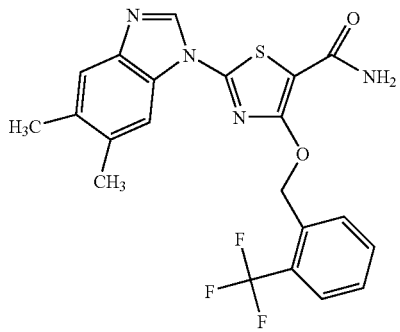

Following the procedure described above for the preparation of 2-(1H-benzimidazol-1-yl)-4-({[2-(trifluoromethyl)phenyl]methyl}oxy)-1,3-thiazole-5-carboxamide using the following materials: 2-chloro-4-({[2-(trifluoromethyl)phenyl]methyl}oxy)-1,3-thiazole-5-carboxamide (0.050 g, 0.14 mmol), 5,6-dimethylbenzimidazole (0.012 g, 0.08 mmol), $K_2CO_3$ (0.011 g, 0.08 mmol) and DMF (4 mL). The title compound was afforded by preparative HPLC. $^1$H NMR (400 MHz, $CDCl_3$) δ 8.48 (s, 1H), 7.77 (d, J=7.9 Hz, 1H), 7.70-7.58 (m, 4H), 7.54-7.49 (m, 1H), 6.81 (bs, 1H), 5.82 (s, 2H), 5.60 (bs, 1H), 2.42 (s, 1H), 2.40 (s, 1H). MS m/z 447 (m+1).

EXAMPLE 6

2-[5,6-Bis(methyloxy)-1H-benzimidazol-1-yl]-4-({[2-(trifluoromethyl)phenyl]-methyl}oxy)-1,3-thiazole-5-carboxamide

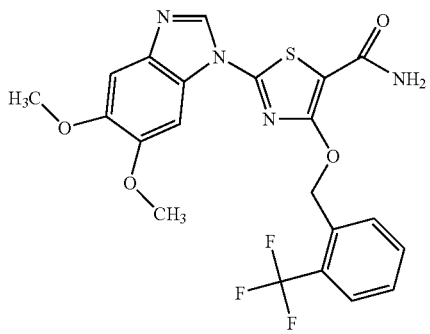

The title compound was prepared in a manner analogous to the procedure described above for the preparation of 2-(1H-benzimidazol-1-yl)-4-({[2-(trifluoromethyl)phenyl]methyl}oxy)-1,3-thiazole-5-carboxamide, using the following materials: 2-chloro-4-({[2-(trifluoromethyl)phenyl]methyl}oxy)-1,3-thiazole-5-carboxamide (0.146 g, 0.434 mmol), 5,6-dimethoxybenzimidazole (0.0851 g, 0.478 mmol), $K_2CO_3$ (0.0720 g, 0.521 mmol) and DMF (4 mL). Flash chromatography afforded 0.114 g (55%) of the title compound. $^1$H NMR (400 MHz, DMSO-$d_6$) δ 8.75 (s, 1H), 7.87-7.73 (m, 4H), 7.61 (m, 1H), 7.61 (s, 1H), 7.37 (s, 1H), 6.94 (br s, 1H), 5.85 (s, 2H), 3.83 (s, 3H), 3.72 (s, 3H). MS m/z 479 (m+1).

EXAMPLE 7

Biological Examples

I. Assay for Inhibition of PLK1

A. Preparation of 6× N-terminal His-tagged PLK kinase domain 6× N-terminal His-tagged PLK kinase domain (amino acids 21-346 preceded by MKKGHHHHHHD (SEQ ID:NO. 1) may be prepared from baculovirus infected T. ni cells under polyhedrin promoter control. All subsequent procedures are performed at 4° C. Cells are lysed in 25 mM HEPES, 200 mM NaCl, 25 mM imidazole; pH 8.0. The homogenate is centrifuged at 14K rpm in a SLA-1500 rotor for 40 min and the supernatant filtered through a 1.2 micron filter. The supernatant is loaded onto a Nickel chelating Sepharose (Amersham Pharmacia) column and washed with 25 mM HEPES, 500 mM NaCl, 25 mM imidazole; pH 8.0. The column is then washed with a 16.6% B step where buffer B is 25 mM HEPES, 500 mM NaCl, 300 mM imidazole; pH 8.0. Protein is eluted using a 10-column volume linear gradient from 16.6% B to 100% B. Fractions were pooled using absorbance at 280 nm. PLK is concentrated using a 10 kDa molecular weight cutoff membrane and then loaded onto a Superdex 75 gel filtration (Amersham Pharmacia) column equilibrated in 25 mM HEPES, 1 mM DTT, 500 mM NaCl; pH 8.0. Protein was pooled by absorbance at 280 nm and then quality controlled using mass spectrometry and SDS-PAGE. PLK was aliquoted and stored at −80° C.

B. Enzyme activity +/− inhibitors was determined as follows: Compounds are added to the plate (1 μl in 100% DMSO). DMSO (5% final) and EDTA (62.5 mM final in 20 μL reaction) are used as controls. Reaction Mix is prepared as follows at 22° C.:

25 mM HEPES, pH 7.2
15 mM MgCl2
1 μM ATP
0.05 μCi/well $^{33}$P-γ ATP (10 Ci/mMol)
1 μM substrate peptide (Biotin-Ahx-SFNDTLDFD) SEQ ID:No. 2.
0.15 mg/ml BSA
1 mM DTT
2 nM PLK1 kinase domain (added last)

Reaction Mix (20 μl) is added per well to each well immediately upon addition of enzyme and incubated 1.25 hrs. at 22° C. The enzymatic reactions are stopped with 50 μl of SPA bead/EDTA mix (50 mM EDTA, 4.0 mg/ml Streptavidin-coated SPA beads in Standard Dulbecco's PBS (without $Mg^{2+}$ and $Ca^{2+}$), 50 μM ATP). Plates are sealed with clear plastic seals, spun at 500×g for 1 min. or settled overnight, and plates counted in Packard TopCount for 30 seconds/well.

C. Results

The data obtained is reported in Table 1 below. In Table 1, +=pIC50<5; ++=pIC50 5-7; +++=pIC50>7.

II. Methylene Blue Growth Inhibition Assay

Normal Human foreskin fibroblasts (HFF) and human colon (HCT116, RKO), lung (H460), prostate (PC3), and breast tumor (MCF7) cell lines are cultured in high glucose DMEM (Life Technologies) containing 10% fetal bovine serum (FBS) at 37° C. in a humidified 10% $CO_2$, 90% air incubator. Cells are harvested using trypsin/EDTA, counted using a haemocytometer, and plated in 100 μl of the appropriate media, at the following densities, in a 96-well tissue culture plate (Falcon 3075): HFF 5,000 cells/well, HCT116 3,000 cells/well, RKO 2,500 cells/well, H460 2,000 cells/well, PC3 8,000 cells/well, MCF7 4,000 cells/well. The next day, compounds are diluted in DMEM containing 100 μg/ml gentamicin, at twice the final required concentration, from 10 mM stock solutions in DMSO. 100 μl/well of these dilutions are added to the 100 μl of media currently on the cell plates. Medium containing 0.6% DMSO is added to control wells. Compounds diluted in DMEM are added to all cell lines. The final concentration of DMSO in all wells is 0.3%. Cells are incubated at 37° C., 10% $CO_2$ for 3 days. Medium is removed by aspiration. Cell biomass is estimated by staining cells with 80 μl per well methylene blue (Sigma M9140, 0.5% in 50:50 ethanol:water), and incubation at room temperature for at least 30 minutes. Stain is removed, and the plates rinsed by immersion in water, and air-dried. To release stain from the cells 100 μl of solubilization solution is added (1% N-lauroyl sarcosine, Sodium salt, Sigma L5125, in PBS), and plates are left at room temperature for about 30 minutes. Optical density at 620 nM is measured on a microplate reader. Percent inhibition of cell growth is calculated relative to vehicle treated control wells. Concentration of compound that inhibits 50% of cell growth ($IC_{50}$) is interpolated using nonlinear regression (Levenberg-Marquardt) and the equation, $y=V_{max}*(1-(x/(K+x)))+Y2$, where Y2=0 and "K" is equal to the $IC_{50}$. The data obtained is reported in Table 1 below.

In Table 1, +=10–>30 μM; ++=1-10 μM: +++=<1 μM.

TABLE 1

| Example | Average pIC50 PLK Enzyme Inhibition | MeB Cell Line | IC50 (μM) |
|---|---|---|---|
| 1 | +++ | H460 | + |
|  |  | HCT116 | + |
|  |  | HFF | + |
|  |  | MCF7 | + |

TABLE 1-continued

| Example | Average pIC50 PLK Enzyme Inhibition | MeB Cell Line | IC50 (μM) |
|---|---|---|---|
|  |  | PC3 | + |
|  |  | RKO | + |
| 2A | +++ | H460 | + |
|  |  | HCT116 | + |
|  |  | HFF | + |
|  |  | MCF7 | ++ |
|  |  | PC3 | + |
|  |  | RKO | ++ |
| 2B | ++ | H460 | + |
|  |  | HCT116 | + |
|  |  | HFF | + |
|  |  | MCF7 | + |
|  |  | PC3 | + |
|  |  | RKO | + |
| 3 | +++ | H460 | + |
|  |  | HCT116 | + |
|  |  | HFF | + |
|  |  | MCF7 | + |
|  |  | PC3 | + |
|  |  | RKO | + |
| 4 | ++ | H460 | + |
|  |  | HCT116 | + |
|  |  | HFF | + |
|  |  | MCF7 | + |
|  |  | PC3 | + |
|  |  | RKO | + |
| 5 | ++ | H460 | + |
|  |  | HCT116 | + |
|  |  | HFF | + |
|  |  | MCF7 | + |
|  |  | PC3 | + |
|  |  | RKO | + |
| 6 | +++ | H460 | ++ |
|  |  | HCT116 | ++ |
|  |  | HFF | + |
|  |  | MCF7 | ++ |
|  |  | PC3 | ++ |
|  |  | RKO | ++ |

That which is claimed is:

1. A compound of formula (I):

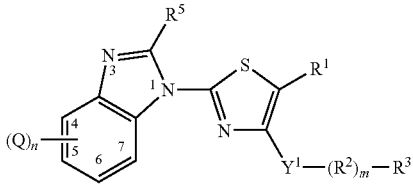

wherein:
R¹ is selected from —C(O)NR⁷R⁸ and —C(S)NR⁷R⁸;
Y¹ is selected from —O—, —S—, —NR⁷—, and —C≡O—;
m is 0 or 1;
n is 0, 1, 2, 3 or 4;
Q is a group of formula: —(R²)ₐ—(Y²)ᵦ—(R²)ᵧ—R⁴; or two adjacent Q groups are selected from the group consisting of alkyl, alkenyl, —OR⁷, —S(O)ᵣR⁷ and —NR⁷R⁸, or together with the carbon atoms to which they are bound, they form a moiety selected from the group consisting of (i) a C₅₋₆cycloalkyl, (ii) C₅₋₆cycloalkenyl, (iii) phenyl, (iv) 5-7 membered heterocycle having 1 or 2 heteroatoms selected from N, O and S, and (v) 5-6 membered heteroaryl having 1 or 2 heteroatoms selected from N, O and S;
a, b and c are the same or different and are each independently 0 or 1;
Y² is selected from —O—, —S(O)ᵣ—, —N(R⁷)—, —C(O)—, —OC(O)—, —CO₂—, —C(O)N(R⁷)—, —C(O)N(R⁷)S(O)₂—, —OC(O)N(R⁷)—, —OS(O)₂—, —S(O)₂N(R⁷)—, —S(O)₂N(R⁷)C(O)—, —N(R⁷)S(O)₂—, —N(R⁷)C(O)—, —N(R⁷)CO₂— and —N(R⁷)C(O)N(R⁷)—;
each R² is the same or different and is independently selected from alkylene, alkenylene and alkynylene;
each R³ and R⁴ is the same or different and is each independently selected from H, halo, alkyl, alkenyl, alkynyl, —C(O)R⁷, —C(O)NR⁷R⁸, —CO₂R⁷, —C(S)R⁷, —C(S)NR⁷R⁸, —C(=NR⁷)R⁸, —C(=NR⁷)NR⁷R⁸, —CR⁷=N—OR⁷, —OR⁷, —S(O)ᵣR⁷, —S(O)₂NR⁷R⁸, —NR⁷R⁸, —N(R⁷)C(O)R⁸, —N(R⁷)S(O)₂R⁸, —NO₂, —CN, —N₃ and a group of formula (ii):

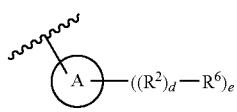

wherein:
Ring A is selected from C₅₋₁₀cycloalkyl, C₅₋₁₀cycloalkenyl, aryl, 5-10 membered heterocycle having 1, 2 or 3 heteroatoms selected from N, O and S and 5-10 membered heteroaryl having 1, 2 or 3 heteroatoms selected from N, O and S;
each d is 0 or 1;
e is 0, 1, 2, 3 or 4;
each R⁶ is the same or different and is independently selected from H, halo, alkyl, alkenyl, alkynyl, cycloalkyl, cycloalkenyl, Ph, Het, —CH(OH)—R²—OH, —C(O)R⁷, —CO₂R⁷, —CO₂—R²—Ph, —CO₂—R²-Het, —C(O)NR⁷R⁸, —C(O)N(R⁷)C(O)R⁷, —C(O)N(R⁷)CO₂R⁷, —C(O)N(R⁷)C(O)NR⁷R⁸, —C(O)N(R⁷)S(O)₂R⁷, —C(S)R⁷, —C(S)NR⁷R⁸, —C(=NR⁷)R⁸, —C(=NR⁷)NR⁷R⁸, —CR⁷=N—OR⁸, =O, —OR⁷, —OC(O)R⁷, —OC(O)Ph, —OC(O)Het, —C(O)NR⁷R⁸, —O—R²—S(O)₂R⁷, —S(O)ᵣR⁷, —S(O)₂NR⁷R⁸, —S(O)₂Ph, —S(O)₂Het, —NR⁷R⁸, N(R⁷)C(O)R⁸, —N(R⁷)CO₂R⁸, —N(R⁷)—R²—CO₂R⁸, —N(R⁷)C(O)NR⁷R⁸, —N(R⁷)—R²—C(O) NR⁷R⁸, —N(R⁷)C(O)Ph, —N(R⁷)C(O)Het, —N(R⁷)Ph, —N(R⁷)Het, —N(R⁷)C(O)NR⁷—R²—NR⁷R⁸, —N(R⁷)C(O)N(R⁷)Ph, —N(R⁷)C(O)N(R⁷)Het, —N(R⁷)C(O)N(R⁷)—R²-Het, —N(R⁷)S(O)₂R⁸, —N(R⁷)—R²—S(O)₂R⁸, —NO₂, —CN and —N₃;
Ph is phenyl optionally substituted from 1 to 3 times with a substituent selected from halo, alkyl, —OH, —R²—OH, —O-alkyl, —R²—O-alkyl, —NH₂, —N(H)alkyl, —N(alkyl)₂, —CN and —N₃;
Het is a 5-7 membered heterocycle having 1, 2, 3 or 4 heteroatoms selected from N, O and S, or a 5-6 membered heteroaryl having 1, 2, 3 or 4 heteroatoms selected from N, O and S, each optionally substituted from 1 to 2 times with a substituent selected from halo, alkyl, oxo, —OH, —R²—OH, —O-alkyl, —R²—O-alkyl, —NH₂, —N(H)alkyl, —N(alkyl)₂, —CN and —N₃;
wherein when Y¹ is —O—, —S— or —NR⁷— and m is 0, then R³ is not halo, —CO₂R⁷, —C(S)R⁷, —C(S)NR⁷R⁸, —C(=NR⁷)R⁸, —C(=NR⁷)NR⁷R⁸, —CR⁷=N—OR⁷, —OR⁷, —S(O)₂NR⁷R⁸, —NR⁷R⁸, —N(R⁷)C(O)R⁸, —N(R⁷)S(O)₂R⁸, —NO₂, —CN or —N₃;
wherein when Q is defined where b is 1 and c is 0, R⁴ is not halo, —C(O)R⁷, —C(O)NR⁷R⁸, —CO₂R⁷, —C(S)R⁷, —C(S)NR⁷R⁸, —C(=NR⁷)R⁸, —C(=NR⁷)NR⁷R⁸, —CR⁷=N—OR⁷, —OR⁷, —S(O)ᵣR⁷, —S(O)₂NR⁷R⁸, —NR⁷R⁸, —N(R⁷)C(O)R⁸, —N(R⁷)S(O)₂R⁸, —NO₂, —CN or N₃;
R⁵ is selected from H, halo, alkyl, cycloalkyl, OR⁷, —S(O)ᵣR⁷, —NR⁷R⁸, —NHC(O)R⁷, —NHC(O)NR⁷R⁸ and —NHS(O)₂R⁷;
f is 0, 1 or 2; and
each R⁷ and each R⁸ are the same or different and are each independently selected from H, alkyl, alkenyl, alkynyl, cycloalkyl and cycloalkenyl;
or a pharmaceutically acceptable salt thereof.

2. The compound according to claim 1, wherein R¹ is —C(O)NR⁷R⁸.

3. The compound according to claim 1, wherein Y¹ is —O—.

4. The compound according to claim 1, wherein m is 0.

5. The compound according to claim 1, wherein R³ is selected from H, alkyl, alkenyl, alkynyl, and a group of formula (ii):

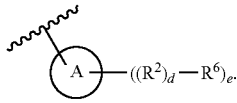

6. The compound according to claim 1, wherein R³ is a group of formula (ii) and Ring A is phenyl.

7. The compound according to claim 1, wherein wherein R³ is a group of formula (ii) and each R⁶ is the same or different and is independently selected from H, halo, alkyl, alkenyl, alkynyl, cycloalkyl, —OR⁷, —S(O)ⱼR⁷, —SO₂NR⁷R⁸, —NR⁷R⁸, —N(R⁷)S(O)₂R⁸, —NO₂ and —CN.

8. The compound according to claim 1, wherein n is 0, 1 or 2.

9. The compound according to claim 1, wherein Q is defined wherein b is 1 and Y² is —O—, —S(O)ⱼ— or —N(R⁷)—.

10. The compound according to claim 1, wherein each R⁴ is the same or different and is independently selected from H, halo, alkyl, alkenyl, alkynyl, —C(O)NR⁷R⁸, —OR⁷, —S(O)ⱼR⁷, —S(O)₂NR⁷R⁸, —NR⁷R⁸, —N(R⁷)C(O)R⁸, —N(R⁷)S(O)₂R⁸, —NO₂, —CN, —N₃ and a group of formula (ii):

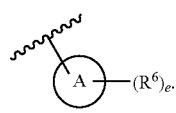

ii

11. The compound according to claim 1, wherein R⁵ is H.
12. A compound selected from the group consisting of:
2-(1H-Benzimidazol-1-yl)-4-({[2-(trifluoromethyl)phenyl]methyl}-oxy)-1,3-thiazole-5-carboxamide;
2-(6-Chloro-1H-benzimidazol-1-yl)-4-({[2-(trifluoromethyl)phenyl]methyl}oxy)-1,3-thiazole-5-carboxamide;
2-(5-chloro-1H-benzimidazol-1-yl)-4-({[2-(trifluoromethyl)phenyl]methyl}oxy)-1,3-thiazole-5-carboxamide;
2-(6-Methoxy-1H-benzimidazol-1-yl)-4-({[2-(trifluoromethyl)phenyl]methyl}oxy)-1,3-thiazole-5-carboxamide;
2-(5-methoxy-1H-benzimidazol-1-yl)-4-({[2-(trifluoromethyl)phenyl]methyl}oxy)-1,3-thiazole-5-carboxamide;
2-(6-Fluoro-1H-benzimidazol-1-yl)-4-({[2-(trifluoromethyl)phenyl]methyl}oxy)-1,3-thiazole-5-carboxamide;
2-(5,6-Dimethyl-1H-benzimidazol-1-yl)-4-({[2-(trifluoromethyl)phenyl]methyl}oxy)-1,3-thiazole-5-carboxamide; and
2-[5,6-Bis(methyloxy)-1H-benzimidazol-1-yl]-4-({[2-(trifluoromethyl)phenyl]-methyl}oxy)-1,3-thiazole-5-carboxamide,
and pharmaceutically acceptable salts thereof.

13. A pharmaceutical composition comprising a compound according to claim 1.

14. The pharmaceutical composition according to claim 13 further comprising a pharmaceutically acceptable carrier, diluent or excipient.

15. The pharmaceutical composition according to claim 14 further comprising a chemotherapeutic agent.

16. A method for reducing the symptoms of a neoplasm susceptible to PLK in an animal, said method comprising administering to the animal a therapeutically effective amount of a compound according to claim 1, wherein said neoplasm is selected from breast cancer, colon cancer, lung cancer, and prostate cancer.

17. A process for preparing a compound according to claim 1, said process comprising the steps of:
a) reacting a compound of formula (III):

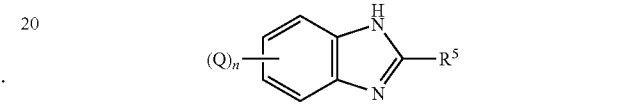

III with a compound of formula (IV):

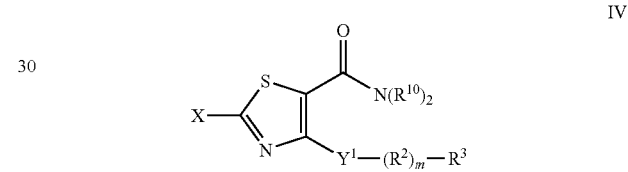

IV wherein:
X is Cl, Br or I;
each R¹⁰ is the same or different and is selected from H, alkyl, alkenyl, alkynyl, cycloalkyl and cycloalkenyl;
to prepare a compound of formula (I);
b) optionally converting the compound of formula (I) to a pharmaceutically acceptable salt thereof; and
c) optionally converting the compound of formula (I) or a pharmaceutically acceptable salt thereof to a different compound of formula (I) or a pharmaceutically acceptable salt thereof.

* * * * *

SEQUENCE LISTING

```
<160> NUMBER OF SEQ ID NOS: 2

<210> SEQ ID NO 1
<211> LENGTH: 11
<212> TYPE: PRT
<213> ORGANISM: baculovirus infected T.ni cells

<400> SEQUENCE: 1

Met Lys Lys Gly His His His His His His Asp
1               5                   10

<210> SEQ ID NO 2
<211> LENGTH: 9
<212> TYPE: PRT
<213> ORGANISM: Artificial Sequence
<220> FEATURE:
<223> OTHER INFORMATION: optimized PLK peptide substrate

<400> SEQUENCE: 2

Ser Phe Asn Asp Thr Leu Asp Phe Asp
1               5
```